United States Patent [19]
Lam

[11] Patent Number: 6,166,003
[45] Date of Patent: Dec. 26, 2000

[54] HETEROCYCLIC COMPOUNDS FOR CANCER CHEMOPREVENTION

[75] Inventor: Luke K. T. Lam, North Oaks, Minn.

[73] Assignee: LKT Laboratories, Inc., St. Paul, Minn.

[21] Appl. No.: 09/251,559

[22] Filed: Feb. 17, 1999

[51] Int. Cl.$^7$ ............... A61K 31/381; A61K 31/341; C07D 307/34; C07D 333/26; C07D 345/00
[52] U.S. Cl. ............... 514/183; 514/438; 514/471; 540/1; 549/75; 549/495
[58] Field of Search ............... 540/1; 549/75, 549/495; 514/183, 438, 471

[56] References Cited

U.S. PATENT DOCUMENTS

| | | | |
|---|---|---|---|
| 2,905,701 | 9/1959 | Nutting et al. | 549/467 |
| 3,725,030 | 4/1973 | Newallis et al. | 549/75 X |
| 3,740,435 | 6/1973 | Newallis et al. | 514/471 |
| 4,938,949 | 7/1990 | Borch et al. | 514/476 |
| 5,126,129 | 6/1992 | Wiltrout et al. | 424/85.2 |
| 5,144,969 | 9/1992 | Chung et al. | |
| 5,231,209 | 7/1993 | Chung et al. | 558/17 |
| 5,411,986 | 5/1995 | Cho et al. | 514/514 |

FOREIGN PATENT DOCUMENTS

WO 94/19948  9/1994  WIPO.

OTHER PUBLICATIONS

Antoš "4–Substituierte β–Phenyläthylisothiocyanate," *Coll. Czch. Chem. Commun.* 37:3339–3341 (1972).
Bird et al., "Aberrant crypts, putative precancerous lesions, in the study of the role of diet in the aetiology of colon cancer," *Cancer Surveys* 8:189–200 (1989).
Bird, "Oberservation and Quantification of Aberrant Crypts in the Murine Colon Treated with a Colon Carcinogen: Preliminary Findings," *Cancer Letters* 37:147–151 (1987).
Boone et al. "Identification of Candidate Cancer Chemopreventive Agents and Their Evaluation in Animal Models and Human Clinical Trials: A Review," *Cancer Res.* 50:2–9 (1990).
Ellman "Tissue Sulfhydryl Groups," *Arch. Biochem. Biophys.* 82:70–77 (1959).
Habig et al., "Glutathione S–Transferases," *J. Biol. Chem.* 249:7130–7139 (1974).
Hecht et al., "Comparative Tumorigenicity and DNA Methylation in F344 Rats by 4–(Methylnitrosamino)–1–(3–pyridyl)–1–butanone and N–Nitrosodimethylamine," *Cancer Res.* 46:498–502 (1986).
Hecht et al. "Rapid single–dose model for lung tumor induction in A/J mice by 4–(methylnitrosamino)–1–(3–pyridyl)–1–butanone and the effect of diet," *Carcinogenesis* 10:1901–1904 (1989).
Jacob et al., "Rat liver microsomal ring– and S–oxidation of thiaarens with central or peripheral thiophene rings," *Toxicology* 67:181–194 (1991).
Jakoby et al. "The Enzymes of Detoxication," *J. Biol. Chem.* 265:20715–20718 (1990).

Jiao et al. "Structure–Activity Relationships of Isothiocyanates as Mechanism–based Inhibitors of 4–(Methylnitrosamino)–1–(3–pyridyl)–1–butanone–induced Lung Tumorigenesis in A/J Mice" *Cancer Res.* 54:4327–4333 (1994).
Kensler et al., "Mechanism of Protection against Aflatoxin Tumorigenicity in Rats Fed 5–(2–Pyrazinyl)–4–methyl–1, 2–dithiol–3–thione (Oltipraz) and Related 1,2–Dithiol–3–thiones and 1,2–Dithiol–3–ones," *Cancer Res.* 47:4271–4277 (1987).
Lam et al., "Inhibition of Benzo[α]pyrene–Induced Forestomach Neoplasia in Mice by Citrus Limonoids," *Nutr. Cancer* 12:43–47 (1989).
Lam et al. "Inhibition of Chemically Induced Carcinogenesis by 2–n–Heptylfuran and 2–n–Butylthiophene from Roast Beef Aroma," *Sulfur Compounds in Foods*, Chap. 22, American Chemical Society (1994).
Lam et al. "Inhibitory Effects of 2–n–Heptylfuran and 2–n–Butylthiophene on Benzo[α]Pyrene–Induced Lung and Forestomach Tumorigenesis in A/J Mice," *Nutr. Cancer* 17:19–26 (1992).
Lam et al., "Reduction of aberrant crypt formation in the colon of CF1 mice by potential chemopreventive agents," *Carcinogenesis* 12:2311–2315 (1991).
Lowry et al. "Protein Measurement with the Folin Phenol Reagent," *J. Biol. Chem.*, 193:265–275 (1951).
Marmur, "A Procedure for the Isolation of Deoxyribonucleic Acid from Micro–organisms," *Mol. Biol.* 3:208–218 (1961).
Morse et al., "Effects of alkyl chain length on the inhibition of NNK–induced lung neoplasia in A/J mice by arylalkyl isothiocyanates," *Carcinogenesis* 10:1757–1759 (1989).
Morse et al., "Effects of Aromatic Isothiocyanates on Tumorigenicity, O$^6$–Methylguanine Formation, and Metabolism of the Tobacco–specific Nitrosamine 4–(Methylnitrosamino)–1–(3–pyridyl)–1–butanone in A/J Mouse Lung," *Cancer Res.* 49:2894–2897 (1989).
Morse et al. "Inhibition of 4–(Methylnitrosamino)–1–(3–pyridyl)–1–butanone–induced DNA Adduct Formation and Tumorigenicity in the Lung of F344 Rats by Dietary Phenethyl Isothiocyanate," *Cancer Res.* 49:549–553 (1989).
Morse et al., "Structure–Activity Relationships for Inhibition of 4–(Methylnitrosamino)–1–(3–pyridyl)–1–butanone Lung Tumorigenesis by Arylalkyl Isothiocyanates in A/J Mice," *Cancer Res.* 51:1846–1850 (1991).

(List continued on next page.)

*Primary Examiner*—Fiona T. Powers
*Attorney, Agent, or Firm*—Mueting, Raasch & Gebhardt, P.A.

[57] ABSTRACT

A compound comprising a heterocyclic moiety, such as a thiophene, covalently attached to an alkylene isothiocyanate moiety. The compound is effective to prevent the occurrence or progression of cancer or a precancerous condition, and can be used for therapeutic or prophylactic purposes. The compound can be provided and administered in the form of a pharmaceutical composition, a cosmetic, a food additive, supplement, or the like. Methods for synthesis and use of the chemopreventive compound of the invention are also provided.

31 Claims, No Drawings

OTHER PUBLICATIONS

Murphy et al., "Rat Liver Metabolism of Benzo[b]naphtho[2,1-d]thiophene," *Chem. Res. Toxicol.* 5:491–495 (1992).

Pozharisski, "Tumours of the Intestines," *Pathology of Tumours in Laboratory Animals,* Second Edition 1:159–198 (1990).

Prochaska et al., "Regulatory Mechanisms of Monofunctional and Bifunctional Anticarcinogenic Enzyme Inducers in Murine Liver," *Cancer Res.* 48:4776–4782 (1988).

Rao et al., "Enhancement of Experimental Colon Carcinogenesis by Dietary 6–Phenylhexyl Isothiocyanate," *Cancer Res.* 55:4311–4318 (1995).

Rouseff et al., "Determination of Limonin and Related Limonoids in Citrus Juices by High Performance Liquid Chromatography," *Anal. Chem.* 52:1228–1233 (1980).

Siller–Cepeda et al., "High Performance Liquid Chromatography Analysis of Reduced and Oxidized Glutathione in Woody Plant Tissues," *Plant Cell Physiology* 32:1179–1185 (1991).

Stoner et al., "Enhancement of esophageal carcinogenesis in male F344 rats by dietary phenylhexyl isothiocyanate," *Carcinogenisis* 16;2473–2476 (1995).

Verma et al., "Effects of dose and duration of treatment with the tumor–promoting agent, 12–O–tetradecanoylphorbol–13–acetate on mouse skin carcinogenesis," *Carcinogenesis* 1–271–276 (1980).

Verma et al., "Modulation of mouse skin tumor promotion by dietary 13–cis–retinoic acid and α–difluoromethylornithine," *Carcinogenesis* 7:1019–1023 (1986).

Wattenberg, "Inhibition of Carcinogenic Effects of Polycyclic Hydrocarbons by Benzyl Isothiocyanate and Related Compounds," *Natl. Cancer Inst.* 58:395–398 (Feb. 1977).

Wattenberg, "Inhibition of Carcinogen–induced Neoplasia by Sodium Cyanate, tert–Butyl Isocyanate, and Benzyl Isothiocyanate Administered Subsequent to Carcinogen Exposure," *Cancer Res.* 41:2991–2994 (Aug. 1981).

Wattenberg et al., "Inhibitors of Colon Carcinogenesis," *Cancer* 40:2432–2435 (Suppl. Nov. 1977).

Wattenberg et al. "Inhibitory effects of 5–(2–pyrazinyl)–4–methyl–1,2–dithiol–3–thione (Oltipraz) on carcinogenesis induced by benzo[a]pyrene, diethylnitrosamine and uracil mustard," *Carcinogenesis* 7:1379–1381 (1986).

Wattenberg "Inhibitory effects of benzyl isothiocyanate administered shortly before diethylnitrosamine or benzo[α] pyrene on pulmonary and forestomach neoplasia in A/J mice," *Carcinogenesis* 8:1971–1973 (1987).

Wilkstrom et al. "Detection of *Porphyromonas gingivalis* in Gingival Exudate by a Dipeptide–Enchanced Trypsin–Like Activity," *J. Periodontal.* 65:7–55 (1994).

Antos et al., Chemical Abstracts, 78:147784, 1973.

Komanova et al., Chemical Abstracts, 79:5196, 1973.

Davies et al., Chemical Abstracts, 84:105431, 1976.

Davies et al., Chemical Abstracts, 88:136480, 1978.

A. Jurasek, Abstract No. 48213p, "5–Nitrofurfuryl isothiocyanate." *Chemical Abstract*, 77:(7) (Aug. 14, 1972).

A Jurášek° et al., "Furan Derivatives. XL. Synthesis of 5–Nitro–2–Substituted Furans on the Basis of 5–Nitrofurfuryl Nitrate," *Collection Czechoslov. Chem.Commun.*, 37:3144–3147 (1972).

E. Komanová et al., "Furan Derivatives. XXXVI. Chromatographic Determination of Some Phenylfuran Derivatives," *Chem. Zvesti*, 27:(1) 112–113 (1973).

A. Krutošíková et al., "Furan Derivatives. XXXV. Preparation of Substituted 5–phenyl–2–furfuryl Bromides, Isothiocyanates, and Thiocyanates," *Chem. Zvesti*, 27:(1) 107–111 (1973).

J. McCarthy et al., "1–(Thienylalkyl)imidazole–2(3H)–thiones as Potent Competitive Inhibitors of Dopamine β–Hydroxylase," *J. Med Chem.*, 33: 1866–1873 (1990).

K. Takahashi et al., "Proton Magnetic Resonance Spectra of Some Thenyl Derivatives, " *Bull. Chem. Soc. Jpn.*, 36: 108–112 (1963).

HETEROCYCLIC COMPOUNDS FOR CANCER CHEMOPREVENTION

STATEMENT OF GOVERNMENT RIGHTS

This invention was made with government support under grant numbers 1 R43 CA62707-01A1 (Phase I) and 2 R44 CA62707-02A1 (Phase II) from the National Institutes of Health (National Cancer Institute). The U.S. government has certain rights in this invention.

BACKGROUND OF THE INVENTION

Chemoprevention is the use of chemicals to prevent the occurrence and/or the progression of cancer. Numerous naturally occurring and synthetic compounds have been found to protect laboratory animals from chemically induced tumorigenesis. A few of the promising ones are on clinical trial as human cancer chemopreventive agents (see, e.g., Boone, C. W., Kelloff, G. J. and Malone, W. E *Cancer Res.* 50:2–9 (1990)). However, most of the inhibitors of carcinogenesis are still at the experimental stage of development. Their inhibitory effects on tumorigenesis vary greatly. Many potent inhibitors, after careful scrutiny, have been found to exhibit side effects that preclude further development as human cancer chemopreventatives. A need, therefore, exists to search for inhibitors of carcinogenesis with low or no toxicity, that may be developed into chemopreventive agents for long term human use.

Two classes of enzymes are known to be associated with xenobiotic metabolism. Phase I enzymes functionalize xenobiotic compounds, usually by way of oxidation or reduction. Although their primary role is to detoxify xenobiotics, several phase I enzymes are also known to activate procarcinogens to yield highly reactive carcinogens. Phase II enzymes conjugate functionalized products with endogenous ligands (e.g., glutathione and sulfate) and serve primarily a detoxification role (Jakoby et al., *J. Biol. Chem.,* 265:20715–20718 (1990)). Compounds that induce or enhance the activity of phase II enzymes represent an important class of chemopreventive agents.

A large portion of the effort in the discovery of chemopreventive agents has been devoted to natural products. Research directed toward the development of synthetic compounds prepared using the rationale of structure-activity relationships (SAR) has also been fruitful in expanding the list of potentially useful agents. Synthetic compounds such as phenyl alkyl isothiocyanates (PAITCs) (M. Morse et al., *Cancer Res.* 51:1846–1850 (1991)), OLTIPRAZ (L. Wattenberg et al., *Carcinogenesis,* 7, 1379 (1986); T. Kensler et al., *Cancer Res.* 47:4271(1987)), and difluoromethylornithine (A. Verma et al., Carcinogenesis, 7:1019 (1986); A. Verma et al., *Carcinogenesis* (Lond.). 1:271 (1980); H. Prochaska et al., *P. Cancer Res.* 48:4776 (1988)) have been found to have cancer prevention potential. For example, chemopreventive compounds derived from sulforaphane ((−)1-isothiocyanato-(4R)-(methylsulfinyl)butane) are described in U.S. Pat. No. 5,411,986 (Cho et al., issued May 2, 1995); and long chain arylalkyl isothiocyanates that inhibit lung tumor formation induced by exposure to tobacco-specific nitrosamine are described in U.S. Pat. No. 5,231,209 (Chung et al., issued Jul. 27, 1993).

Plant isothiocyanates (ITCs) occur naturally as glucosinolates in cruciferous vegetables. These glucosinolates are subjected to enzymatic hydrolysis by myrosinase during the processing or digestion of foods to yield the corresponding isothiocyanates. Benzyl isothiocyanate, phenethyl isothiocyanate, allyl isothiocyanate, and sulforaphane have been found in cruciferous vegetables that include kale, cabbage, Brussels sprouts, cauliflower, broccoli, and turnips. These natural isothiocyanates are well known phase II enzyme inducers and inhibitors of tumorigenesis induced by polycyclic aromatic hydrocarbons or nitrosamines in several different animal models. Phenethyl isothiocyanate is the hydrolysis product of gluconasturtiin, an abundant natural product present in cruciferous vegetables. Because of its relatively low toxicity, albeit less outstanding inhibitory activity in tumorigenesis studies, it is being considered for Phase I clinical trial. Synthetic PAITCs with the alkylene chain longer than ethylene have been found to improve upon the potency of these compounds as inhibitors of NNK-induced carcinogenesis (M. Morse et al., Cancer Res. 51:1846–1850 (1991); J. Ding et al., *Cancer Res.* 54:4327–4333 (1994)). Carbon chain length from 3 to 12 in this series have been examined, and all appear to have inhibitory activity.

SUMMARY OF THE INVENTION

The compound of the invention is a 5-membered heterocyclic ring substituted with an alkylene isothiocyanate at one or more of the 2-, 3- and 5-positions, as shown in Formula I:

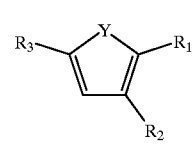

I wherein:
$R_1$ is H or (alkylene)-NCS;
$R_2$ is H or (alkylene)-NCS;
$R_3$ is H, (alkylene)-NCS, or a blocking group; and
Y is S, O or Se;
provided that at least one of $R_1$, $R_2$ and $R_3$ is (alkylene)-NCS.

The term "alkylene" as used herein means a divalent saturated hydrocarbon chain containing one or more carbon atoms. An alkylene can be linear or branched. Examples of linear alkylenes include methylene (—$CH_2$—), ethylene (—$CH_2$—$CH_2$—), propylene (—$CH_2$—$CH_2$—$CH_2$—), butylene (—$CH_2$—$CH_2$—$CH_2$—$CH_2$—) and so on. Examples of branched alkylenes include compounds such as —$CH_2$—CH($CH_3$)—$CH_2$—, —$CH_2$—CH($CH_2CH_3$)—$CH_2$—, $CH_2$—CH($CH_3$)—$CH_2$—CH($CH_3$)—$CH_2$—, —$CH_2$—C($CH_3$)$_2$—$CH_2$— and the like. The compound of the invention is not intended to be limited by the length of the alkylene chain that connects an isothiocyanate (—NCS) group to the heterocyclic moiety. Moreover, where the compound contains an alkylene isothiocyanate substituent at more than one position on the heterocyclic ring, the alkylene functionalities connecting the isothiocyanate groups at the respective ring positions can have different numbers of carbon atoms. Linear alkylene chain lengths of about 1 to about 20 carbons ($C_1$–$C_{20}$) are preferred for ease of synthesis. Preferably, the alkylene chain length connecting the isothiocyanate group to the heterocyclic moiety is about 1 to about 12 carbons ($C_1$–$C_{12}$), more preferably about 1 to about 6 carbons ($C_1$–$C_6$), most preferably about 1 to about 4 carbons ($C_1$–$C_4$). For example, a representative compound of the invention is 2-thienyl butyl isothiocyanate, which has a $C_4$ alkylene functionality (i.e., a 4 carbon chain) connecting the isothiocyanate (—NCS) to the 2-position of the thienyl ring (I, wherein $R_1$=($CH_2$)$_4$NCS; $R_2$=H; $R_3$=H; and Y=S).

As used herein, the term "heterocyclic ring" refers to a ring structure that contains as a member of the ring at least one noncarbon atom. In the heterocyclic ring of the compound of formula I, the non-carbon member Y is preferably S, but can alternatively be O or Se.

At least one of $R_1$, $R_2$ and $R_3$ of the compound of formula I is (alkylene)-NCS. Where $R_1$ is (alkylene)-NCS, $R_2$ is preferably H; and where $R_2$ is (alkylene)-NCS, $R_1$ is preferably H. A mono-substituted compound is preferred for ease of synthesis, but the compound of the invention can nonetheless contain up to three alkylene isothiocyanate substituents, at any of the 2-, 3- and 5-positions on the heterocyclic ring.

$R_3$ can be H, (alkylene)-NCS, or a blocking group. Where $R_3$ is a blocking group, it is not intended to be limited to any particular blocking group. The blocking group can be aromatic or aliphatic, and can be linear, branched, or cyclic. Blocking the 5-position of the ring is desirable in order to enhance the chemopreventive effect of the compound of the invention, for example by slowing metabolism of the ring moiety in a treated subject or by way of a steric effect. The blocking group is preferably an alkyl, aryl, alkoxy, alkylmercapto, alkylene aryl, arylalkyl, aryloxy, $CX_3$, or X; wherein X is F, Cl, or Br. Aromatic or aliphatic constituents of a blocking group can be substituted or unsubstituted. More preferably the blocking group is $CH_3$, $OCH_3$, $SCH_3$, $CX_3$ or X; most preferably it is $OCH_3$, $SCH_3$, $CF_3$ or F.

Also included in the present invention is a method for making a compound having formula I. For example, to make a mono-substituted (2- or 3-substituted) heterocyclic alkylene isothiocyanate, the starting material is a 5-membered heterocyclic ring (i.e., thiophene or the analogous furyl- or seleno-heterocycle) that is substituted at the 2- or 3-position with an alkylene bromide, and, optionally, at the 5-position with a blocking group (IIIc):

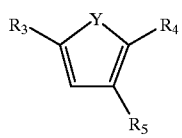

IIIc wherein $R_3$ is H or a blocking group, one of $R_4$ and $R_5$ is H; and the other of $R_4$ and $R_5$ is (alkylene)-Br.

This method involves substituting the bromide (—Br) with an amine (—$NH_2$) to create a nucleophilic 2- or 3-alkylene amine intermediate, respectively, followed by reacting the alkylene amine with thiophosgene to yield a mono-substituted compound according to formula I wherein one of $R_1$ and $R_2$ is H; the other of $R_1$ and $R_2$ is (alkylene)-NCS, $R_3$ is H or a blocking group; and Y is S, O, or Se.

The synthetic method can also be used to make a 2,5 disubstituted heterocyclic alkylene isothiocyanate where the starting material is a 5-membered heterocyclic ring (i.e., thiophene or the analogous furyl- or seleno-heterocycle) that is substituted at the 2- and 5-positions with an alkylene bromide:

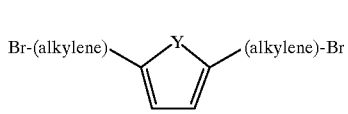

IIId

This method involves substituting each bromide (—Br) with an amine (—$NH_2$) to create a nucleophilic disubstituted alkylene amine intermediate, followed by reacting the disubstituted alkylene amine intermediate with thiophosgene to yield a disubstituted compound according to formula I wherein $R_1$ and $R_3$ are each (alkylene)-NCS; $R_2$ is H; and Y is S, O or Se.

In a preferred embodiment of the method of the invention, the bromide is replaced by an amine by treating the starting material IIIc or IIId with a reagent, for example a phthalimide salt, such as potassium or sodium phthalimide, to yield the corresponding secondary or tertiary amine, such as a mono- or disubstituted N-phthalimidoalkylene intermediate, respectively, then treated with hydrazine to yield the corresponding alkylene amine intermediate. The mono- or disubstituted alkylene amine intermediate is then treated with thiophosgene to yield a compound according to formula I. In another preferred embodiment, the bromide is replaced by an azide by treating the starting material with an azide salt, such as sodium or potassium azide, to yield the corresponding alkylene azide intermediate, then reducing the mono- or disubstituted alkylene azide intermediate with sodium borohydride to yield the corresponding alklyene amine.

The present invention further includes a pharmaceutical composition comprising an active ingredient which is a compound of the present invention. Preferred embodiments of the pharmaceutical composition are those that contain preferred embodiments of the compound having formula I, as set forth above. Included in the pharmaceutical composition is, preferably, a pharmaceutically acceptable carrier, which can comprise a pharmaceutically acceptable salt. The pharmaceutical composition is suitable for treatment of an existing condition or for prophylactic use.

Additionally, the compound of the present invention can be incorporated into food or drink as an additive or supplement, or formulated for cosmetic use, as in a body lotion, crème, sunscreen or the like.

The present invention further includes a method for preventing the occurrence or progression of a cancer or a precancerous condition, including cellular changes characterized by neoplasia. The method comprises administering to a mammal a chemopreventive composition comprising the compound the present invention in an amount effective to prevent the occurrence of cancer (carcinogenesis) or a precancerous condition, or to slow or halt the progression of cancer or precancerous conditions. The chemopreventive composition can be administered as a therapeutic to treat an existing condition or as a prophylactic in advance of exposure to a carcinogenic compound or event.

DETAILED DESCRIPTION

The present invention is directed toward 5-membered heterocyclic isothiocyanates, their synthesis, and their use as cancer chemopreventive agents. Phenyl alkyl isothiocyanates (PAITCs, also referred to herein as phenyl alkylene isothiocyanates) are known inhibitors of lung cancer, with phenyl butyl isothiocyanate (PBITC, also referred to herein as phenyl butylene isothiocyanate) being one of the most well-studied of the series (M. Morse et al., *Cancer Res.* 51:1846–1850 (1991)). Structure/activity studies from the laboratory of Dr. Fung-Lung Chung indicated that PAITCs having alkyl chain lengths of up to 12 carbons (the highest number studied) were active as inhibitors of NNK-induced lung tumorigenesis (D. Jiao et al., *Cancer Res.* 54: 4327–4333 (1994)). Interestingly, they found that compounds with alkyl chain lengths longer than 6 carbons were more active inhibitors of lung tumorigenesis than those of shorter chain lengths.

Although PAITCs have thus been shown to be inhibitory of carcinogenesis in the lung, at least one member of the series, phenyl hexyl isothiocyanate (PHITC, also referred to herein as phenyl hexylene isothiocyanate) has been shown to have the opposite effect in colon cells. When administered with azoxymethane, a known carcinogen, this PHITC increases the number of colon tumors, thereby functioning as a co-carcinogen rather than a chemopreventive agent (C. Rao et al., *Cancer Res.* 55:4311–4318 (1995)). Additionally, PHITC has been shown to enhance esophageal carcinogenesis in male rats when co-administered with the carcinogen N-nitrosomethylbenzylamine (G. D. Stoner et al., *Carcinogenisis* 16:2473–2476 (1995)).

The heterocyclic compound 2-n-butyl thiophene (2BT) has also been shown to be an inhibitor of carcinogenesis. Furan- and thiophene-containing natural products are ubiquitous in nature. 2BT and 2-n-heptylfuran (HF) are two of many thiophenes and furans found in cooked meat. Similar to other furan-containing natural products, such as kahweol, limonin and nomilin, 2BT and HF were found to induce increased glutathione sulfotransferase (GST) activity in various tissues in mice. In addition to the induction of the phase II detoxifying enzyme GST, the level of the corresponding mandatory substrate, GSH, was also enhanced. These two phenomena are considered favorable for the detoxification of carcinogens. Using animal tumor models with different carcinogens, it has been determined that 2BT inhibits tumorigenesis in the forestomach, lung and colon of mice as well as the precancerous lesions, aberrant crypts, in the colon of mice (see L. Lam et al., *Nutr. Cancer* 17:19–26 (1992), which is incorporated by reference in its entirety as if fully set forth herein). 2BT is particularly active in the colon.

An object of the present invention is to provide a chemopreventive compound that has less toxicity, superior activity as an enzyme inducer, and broader inhibitory activity than either PBITC or 2BT. Although the planar five membered ring of the present compound is close in size to the size of the benzene ring in PBITC, the electronic character of the heterocyclic ring structure (for example, in the thiophene, due to the polarizable sulfur atom) is quite different from that of benzene. Nonetheless, prototype compounds such as 2-thienylmethylisothiocyanate (2-TMITC), 3-thienylmethylisothiocyanate (3-TMITC), 2-thienylbutylisothiocyanate (2-TBITC) and 3-thienylbutylisothiocyanate (3-TBITC) were found to have enzyme inducing activity similar to, or greater than, phenyl butyl isothiocyanate (PBITC) or 2-butyl thiophene (2BT). It should be noted that although compounds of the invention are sometimes referred to herein as heterocyclic "alkyl isothiocyanates" in accordance with terminology in common use in the art, they are more accurately termed "alkylene isothiocyanates" in that a divalent alkylene chain (—$(CH_2)_n$—), e.g., methylene, ethylene, propylene, butylene and so on) functions as a linker between the isothiocyanate (—NCS, linked to the alkylene chain at the nitrogen atom) and the heterocyclic ring according to the invention (see, for example, compounds Ia and Ib). In other words, the terms "alkyl isothiocyanate" and "alkylene isothiocyanate," are used interchangeably herein to mean a —$(CH_2)_n$—NCS substituent; accordingly, for example, methyl isothiocyanate means —$CH_2$—NCS; butyl isothiocyanate means —$(CH_2)_4$—NCS, phenyl butyl isothiocyanate means Ph-$(CH_2)_4$—NCS, and so on.

The potentials of various TAITCs as chemopreventive agents were evaluated using well-known assays for chemopreventive activity including GST induction, NNK-methylation, and AC inhibition assays, as described in the following examples. The tested members of the new class of compounds were found to be potent inducers of the GST enzyme system. Moreover, the prototype TAITCs were found to be active in both the lung and the colon of mice. Surprisingly, the compound of the invention, which differs significantly from both reference compounds PBITC and 2-BT in size, shape, electronic character, and bulkiness, exhibited inhibitory activities comparable to or better than the reference compounds. In addition, unlike PHITC, the compounds of the invention did not act as a co-carcinogen in colon cells.

The 5-membered ring of the compound of the invention can be monosubstituted, disubstituted, or trisubstituted, such that the alkylene isothiocyanate moiety is at one or more of the 2-, 3- or 5-positions on the ring. Where an alkylene isothiocyanate is at either or both of the 2- and 3-positions of the heterocyclic ring, the compound optionally includes a blocking or stabilizing group at the 5-position on the ring (see formula I). The 2-substituted series of compounds, with or without a blocking group at the 5-position, is preferred for use as a chemopreventive agent because it can be synthesized from more readily available starting materials.

In a particularly preferred embodiment, the compound of the invention is a 2,5-disubstituted compound. Thiophene metabolism is believe to occur at the S-atom and the α carbons (2,5-positions) of the molecule (S. Murphy et al., *Chem. Res. Toxic.* 5:491–495 (1992); J. Jacob et al., *Toxicology* 68: 181–194 (1991)). Without wishing to be bound by theory, it is believed that on the 2-monosubstituted series, metabolic conversion of the ring can still occur at the S atom by way of the 5-position. To slow down and prevent the rate of oxidative metabolism of the compound, the 5-position of the 2-TAITC series is preferably blocked by the use of substituents such as $CH_3$, $OCH_3$, $CF_3$ and F groups. In addition to blocking the 5-position, these substituents serve as additional steric hindrance near the S atom. The $OCH_3$, $CF_3$ and F groups are preferred as blocking groups.

The invention provides methods for synthesizing a compound having formula I. In one preferred method (Scheme 1a), 2-(n-bromoalkylene)thiophene (IIIa wherein Y=S; $R_3$ is H or a blocking group; and n is an integer), or the furyl- or seleno-heterocyclic analog thereof (IIIa wherein Y=O or Se), is reacted with a phthalimide salt, preferably potassium phthalimide to yield 2-(n-phthalimidoalkylene)thiophene or the furyl- or seleno-heterocyclic analog thereof (IVa). This compound (IVa) is then reacted with hydrazine and subjected to acid hydrolysis. The resulting n-(2-thienyl)alkylene amine or the furyl- or seleno-heterocyclic analog thereof (Va) is reacted with thiophosgene under alkaline conditions to yield the corresponding compound of the invention (Ia). Optionally, the method includes the formation of IIIa from the corresponding lithium salt (IIa), preferably 2-thienyl lithium (IIa wherein Y=S), by reaction with dibromoalkane having chain length n.

An analogous method for synthesizing a 3-substituted compound (Ib) from 3-(n-bromoalkylene)thiophene (IIIb wherein Y=S; $R_3$ is H or a blocking group; and n is an integer), or the furyl- or seleno-heterocyclic analog thereof (IIIb wherein Y=O or Se) is also provided by the present invention (Scheme 1b). The method optionally includes the formation of IIIb from the corresponding lithium salt (IIb), preferably 3-thienyl lithium (IIb wherein Y=S) by reacting the corresponding 3-bromo-heterocycle (VIb), preferably 3-bromothiophene (VIb wherein Y=S) with n-$(CH_2)^-$ lithium at very low temperature (about −70 C.) to prevent isomerization of the ring, to yield IIb, followed by reacting the lithium salt (IIb) with dibromoalkane having chain length n.

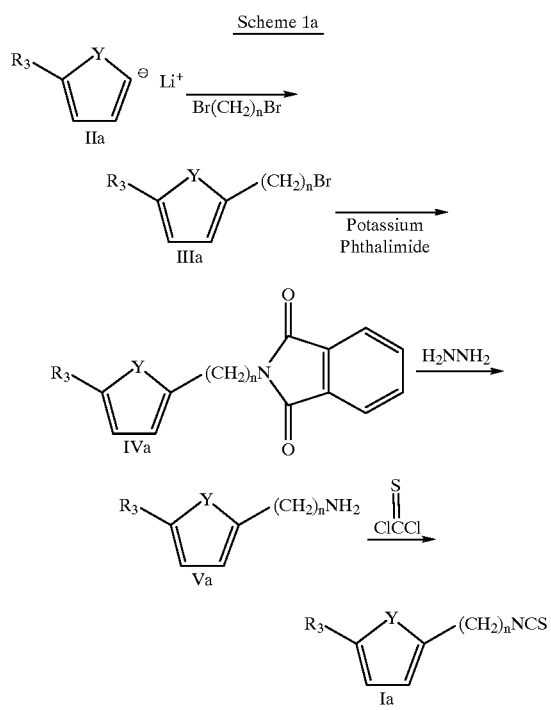

Scheme 1a

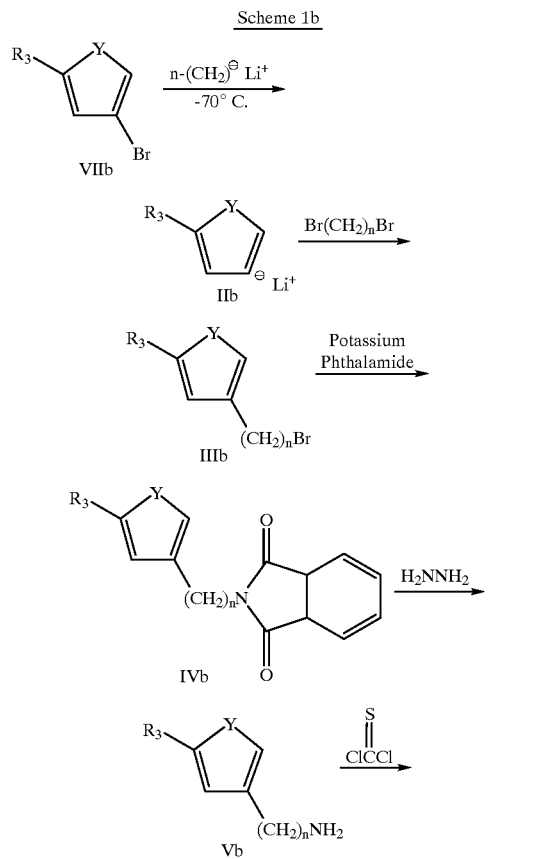

Scheme 1b

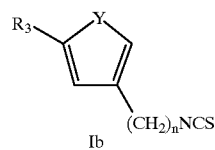

In another preferred method for making the compounds of the invention, (Scheme 2a), 2-(n-bromoalkylenethiophene (IIIa wherein Y=S; $R_3$ is H or a blocking group; and n is an integer), or the furyl- or seleno-heterocyclic analog thereof (IIIa wherein X=O or Se), is reacted with an azide salt, such as sodium azide, instead of a phthalimide salt, to yield the corresponding n-(2-thienyl)alkylene azide or the furyl- or seleno-heterocyclic analog thereof (VIa). This compound (VIa) is then reacted with sodium borohydride to yield the corresponding n-(2-thienyl)alkylene amine (Va). Likewise, a 3-substituted compound of the invention (Ib) can be synthesized via an azide intermediate or the furyl- or seleno-heterocyclic analog thereof (VIb) wherein X=O or Se and n is an integer) in an analogous method (Scheme 2b). These embodiments of the synthetic method optionally include the step of synthesizing IIIa or IIIb, from IIa and IIb, respectively, as described above and shown in Schemes 1a and 1b.

In any of the above-described methods of synthesizing a compound having formula I, the amine (Va or Vb) can, alternatively, be reacted with $CS_2$ in the presence of triethylamine to yield a heterocycle substituted at the 2- or 3-position, respectively, with $—(CH_2)_n—NH—(C=S)—SH.N(CH_3)_3$. Subsequent treatment with $I_2$ yields the heterocyclic alkylene isothiocyanate (Ia or Ib) of the invention.

Scheme 2a

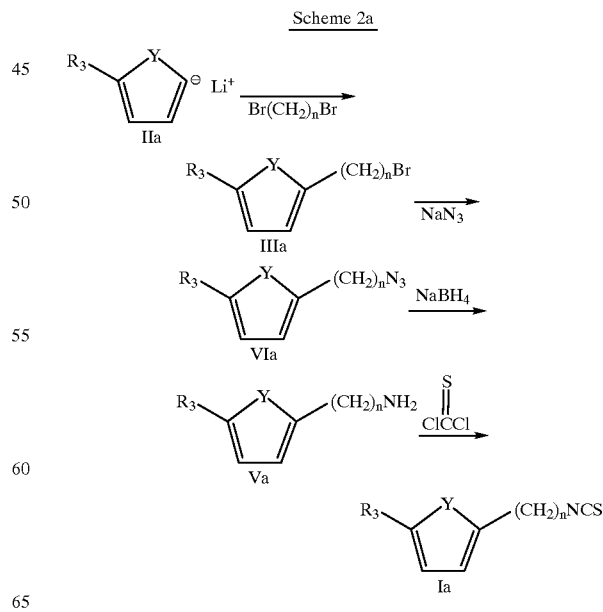

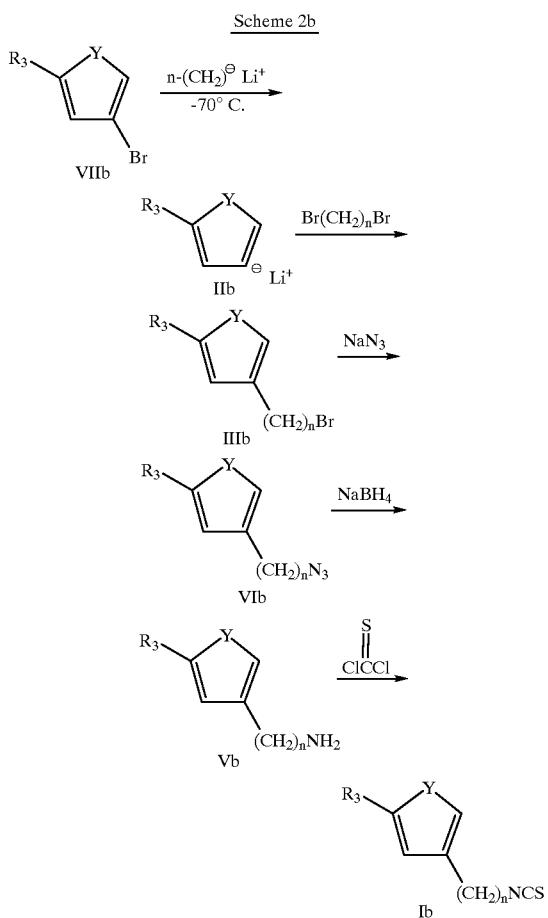

Scheme 2b

The present invention also provides a chemopreventive composition that includes a compound of the invention and, optionally, a pharmaceutically acceptable carrier. The chemopreventive compounds of the present invention are formulated in pharmaceutical compositions and then, in accordance with the method of the invention, administered to a mammal, such as a human patient, in a variety of forms adapted to the chosen route of administration. The formulations include those suitable for oral, rectal, vaginal, topical, nasal, ophthalmic or parental (including subcutaneous, intramuscular, intraperitoneal and intravenous) administration.

The formulations may be conveniently presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into the desired formulations.

Formulations of the present invention suitable for oral administration may be presented as discrete units such as tablets, troches, capsules, lozenges, wafers, or cachets, each containing a predetermined amount of the chemopreventive compound as a powder or granules, as liposomes containing the chemopreventive agent, or as a solution or suspension in an aqueous liquor or non-aqueous liquid such as a syrup, an elixir, an emulsion or a draught. Such compositions and preparations should contain at least about 0.1% active compound. The percentage of the compositions and preparations may be varied and may conveniently be between about 1% to about 60% of the weight of a given unit dosage form. The amount of chemopreventive compound in such therapeutically useful compositions is such that the dosage level will be effective to prevent or suppress the development of cancer in the subject, for example by stimulating the production of phase II enzymes in the subject.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The chemopreventive compound may be incorporated into sustained-release preparations and devices.

The chemopreventive compounds of the invention can be incorporated directly into the food of the mammal's diet, as an additive, supplement, or the like. Thus, the invention further provides a food product containing a chemopreventive compound of the invention. Any food is suitable for this purpose, although processed foods already in use as sources of nutritional supplementation or fortification, such as breads, cereals, milk, and the like, may be more convenient to use for this purpose.

Formulations suitable for parenteral administration conveniently comprise a sterile aqueous preparation of the chemopreventive compound, or dispersions of sterile powders comprising the chemopreventive compound, which are preferably isotonic with the blood of the recipient. Isotonic agents that can be included in the liquid preparation include sugars, buffers, and sodium chloride. Solutions of the chemopreventive compound can be prepared in water, optionally mixed with a nontoxic surfactant. Dispersions of the chemopreventive compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the chemopreventive compound, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the chemopreventive compounds over a prolonged period can be achieved by including agents for delaying, for example, aluminum monostearate and gelatin.

Nasal spray formulations comprise purified aqueous solutions of the chemopreventive compound with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the chemopreventive compound dissolved or suspended in one or more media such as mineral oil, petroleum, polyhydroxy alcohols or other bases used for topical pharmaceutical formulations. The compound of the invention is particularly suited to incorporation in a cosmetic lotion, crème, or sunscreen for use on the skin.

In addition to the aforementioned ingredients, the formulations of this invention may further include one or more accessory ingredients including diluents, buffers, binders, disintegrants, surface active agents, thickeners, lubricants, preservatives (including antioxidants) and the like.

Useful dosages of the compounds of formula I can be determined by comparing their in vitro activity and the in vivo activity in animals models. Methods for extrapolation of effective dosages in mice, and other animals, to humans are known in the art; for example, see U.S. Pat. No. 4,938,949, which is incorporated herein by reference, in its entirety.

Generally the concentration of the compound of formula I in a liquid composition, such as a topical lotion, will be about 0.1 wt-% to about 25 wt-%, preferably about 0.5 wt-% to about 10 wt-% (wt-%, weight percent, means grams of compound per 100 mL liquid). For adult humans, single dosages for injection, infusion, or ingestion will generally vary between about 10–1500 mg, and may be administered, for example about 1 to about 3 times per day, to yield levels of about 0.5 mg to about 50 mg per kg of body weight per day. For example, doses of about 10 to about 600 mg of chemopreventive compound for oral administration, about 10 to about 200 mg of chemopreventive compound for intramuscular injection, and about 10 to about 100 mg of chemopreventive compound for intravenous injection, may be preferably administered. Suitable doses to be administered are, in general, those which are sufficient to produce a chemopreventive effect, such as by inducing a demonstrable increase of phase II enzyme expression. This will typically not exceed 500 micromoles per kg of body weight per day, and may be much lower.

The invention further includes a method of protecting a mammal against the occurrence or progression of a cancer or a precancerous condition comprising administering to a mammal the chemopreventive composition of the invention in an amount effective to produce a cancer preventative effect. A cancer preventative effect includes both prevention of an initial occurrence of cancer (carcinogenesis) or a precancerous condition as well as the prevention of a metastasis of an existing cancer; it also includes slowing, halting, or reversing the progression of an existing cancer or precancerous condition. Accordingly, the chemopreventive composition can be administered as a therapeutic to treat an existing condition or as a prophylactic before, during or after possible or actual exposure to a known or suspected carcinogenic or procarcinogenic compound, event, or agent of any type. A carcinogenic or procarcinogenic compound, event or agent is to be understood to include any mutagenic or potentially mutagenic agent, event, or condition including a mutagenic chemical compound, such as a toxicant; radioactivity, including but not limited to alpha, beta, or gamma emissions from an radioisotope; electromagnetic radiation of any wavelength or frequency, such as x-ray, ultraviolet, or infrared radiation; exposure to a magnetic field or an electromagnetic field (EMF), and the like. Preferably, the chemopreventive compound of the invention is administered prophylactically before, during or after possible or actual exposure to a mutagenic chemical compound.

EXAMPLES

The objects, features and advantages of the present invention illustrated in the following examples, which incorporate particular materials and amounts, should not be construed to unduly limit this invention.

Example I

Synthesis of 2-Thienyl Methyl Isothiocyanate (2-TMITC) From 2-Aminomethyl Thiophene

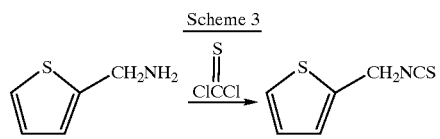

The starting material 2-aminomethyl thiophene was purchased from Lancaster Synthesis (Windham, N.H.). The conversion of the amine to 2-TMITC was carried out according to the procedures of Antos and coworkers shown in Scheme 3 (*Coll. Czch. Chem. Commun.* 37:3339–3341 (1972)). Briefly, the thienyl methyl amine dissolved in water was added dropwise to a solution of thiophosgene in dichloromethane. In another dropping funnel a solution of 10% sodium hydroxide was introduced slowly to maintained alkalinity of the reaction mixture. The reaction was allowed to stand at room temperature for an additional hour with stirring. The organic layer was separated and washed with water, saturated sodium chloride solution, water, and dried over anhydrous magnesium sulfate. The solvent was removed in vacuo and the product obtained by vacuum distillation.

Example II

Synthesis of 2-Thienyl Alkyl Isothiocyanates (2-TAITCs) from 2-Thienyl Lithium via Phthalimide Intermediates

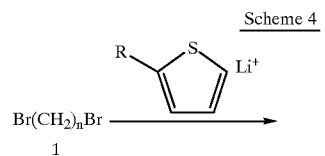

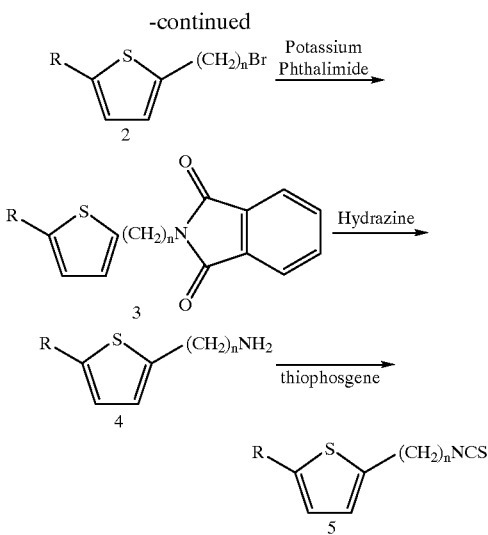

In this method, 2-thienyl alkyl bromide that was generated from 2-thienyl lithium was allowed to react with potassium phthalimide, and the resulting compound was cleaved in the presence of hydrazine to yield the thienyl alkyl amine (Scheme 4). The thienyl alkyl amine was then converted to the corresponding thienyl alkyl isothiocyanate using thiophosgene. This Example sets forth the specific steps used to synthesize compounds 5e (R=H, n=8) and 5h (R=Me, n=4) as shown in the following table; however, analogous methods were used to synthesize mono- and di-substituted TAITCs 5a through 5j, and the results are set forth below.

Mono- and Disubstituted TAITCs

| Compound | R | n | Protocol | Mol. Wt. |
|---|---|---|---|---|
| 5a | H | 2 | T2ITC | 169.3 |
| 5m | H | 3 | T3ITC | 183.3 |
| 5b | H | 4 | T4ITC | 197.0 |
| 5n | H | 5 | T5ITC | 211.0 |
| 5c | H | 6 | T6ITC | 225.4 |
| 5d | H | 7 | T7ITC | 239.4 |
| 5e | H | 8 | T8ITC | 253.4 |
| 5o | H | 9 | T9ITC | 267.4 |
| 5f | H | 10 | T10ITC | 281.5 |
| 5g | H | 12 | T12ITC | 309.5 |
| 5h | $CH_3$ | 4 | MeT4ITC | 211.1 |
| 5i | $CH_3O$ | 4 | MOT4ITC | 226.9 |
| 5j | $CH_3S$ | 4 | MST4ITC | 243 |
| 5k | $CF_3$ | 4 | FMT4ITC | (not yet synthesized) |
| 5l | F | 4 | FT4ITC | (not yet synthesized) |

Step 1a. This procedure was used to synthesize the monosubstituted synthetic intermediate 2-(n-bromoalkyl) thiophenes (2, R=H; i.e., compounds 2a through 2g). The synthesis of 2e was accomplished by adding 2-thienyllithium (0.1 moles) (100 mL, 2.5 M) (Aldrich, Milwaukee, Wis.) dropwise, with stirring, to a well chilled solution of 1,8-dibromooctane (1, n=8) (32.6 gm, 0.12 moles) (Aeros Organics, Pittsburgh, Pa.) in tetrahydrofuran (THF) (100 mL) (Aldrich, Milwaukee, Wis.) under argon. The temperature was maintained at −25° C. (ice-salt bath) for one hour after the addition was complete. The ice-salt bath was removed and the reaction mixture was allowed to warm to room temperature over one hour. The mixture was poured over ice-water (150 mL) and the layers were separated. The aqueous layer was extracted with ethyl acetate (3×100 mL). The combined organic layers were washed with water (3×20 mL), dried over $MgSO_4$ (anhydrous), filtered, and evaporated under reduced pressure. Distillation or column chromatography (silica gel, hexanes; Fischer Chemical Co., Pittsburgh, Pa.) can be used to yield 16 gm of 2-(8-bromo-octyl)thiophene (2e) (58.2%).

Yields (in mass and % of theoretical yield) for syntheses (some of which were performed multiple times) of analogous monosubstituted intermediates (2, R=H) of varying alkyl chain length (n) were as follows:

2-(3-Bromopropyl)thiophene (2m). 27.6 gm (42.5%)

2-(4-Bromobutyl)thiophene (2b). 15 gm (71.1%)

2-(5-Bromopentyl)thiophene (2n). 83.4 gm (74%)

2-(6-Bromohexyl)thiophene (2c). 20 gm (81.3%)

2-(7-Bromoheptyl)thiophene (2d). 4.7 gm (37%), 7 gm (76.9%), 14 gm (91.5%)

2-(9-Bromononyl)thiophene (2o). 34 gm (57%)

2-(10-Bromodecyl)thiophene (2f). 16 gm (52.8%)

2-(12-Bromododecyl)thiophene (2g). 26.3 gm (79.5%), 19 gm (57%)

Step 1b. This procedure was used to synthesize the disubstituted synthetic intermediate 2-(n-bromoalkyl)-5-R-thiophene (2, wherein R is not H). The synthesis of 2h was accomplished by first synthesizing the 2-methylthienyllithium intermediate. A solution of n-butyllithium (2.5 M in hexane) (Aldrich Chemical Co.) (4.4 mL, 0.011 moles) was added dropwise to 2-methylthiophene (0.98 gm, 0.01 moles) (Lancaster Synthesis, Windham, N.H.) in THF (50 mL) at 0° C. to yield the lithium salt of 2-methylthiophene. The solution was stirred at room temperature for one hour. 1,4-Dibromobutane (3.24 gm, 0.015 moles) was added in one lot to the lithium salt of 2-methylthiophene at 0° C. The solution was allowed to warm to room temperature and stirred for 12 hours. Water (20 mL) was added and the layers were separated. The organic layer was diluted with ethyl acetate (50 mL) and washed with water (3×10 mL), dried over MgSO4 (anhydrous), filtered and evaporated under reduced pressure. Purification by column chromatography (silica gel, hexanes) gave 2 gm of 2-(4-bromobutyl)-5-methylthiophene (2h) (85.8%).

Yields for the syntheses of analogous disubstituted intermediates (2, wherein R is not H) of varying alkyl chain length (n) were as follows:

2-(4-Bromobutyl)-5-methoxythiophene (2i) 2.3 gm (93.4%), 20 gm (91.7%)

2-(4-Bromobutyl)-5-methylmercaptothiophene (2j) 9 gm (89.1%)

Step 2. In this step, the mono- or disubstituted synthetic intermediate 2-(n-phthalimidoalkyl)thiophene (3) was synthesized from compound 2. To synthesize 3e, 2-(8-bromooctyl)thiophene (2e) from step 1a (16 gm, 0.058 moles) and potassium phthalimide (10.8 gm, 0.058 moles) were added to acetone (200 mL) and heated under a reflux condenser. The mixture was stirred and refluxed for 48 hours. The cooled mixture was filtered to remove KBr and unreacted starting material. The filtrate was evaporated under reduced pressure to give an oil that solidified on standing. Recrystallization from ethyl acetate/hexane mixture yielded 8.5 gm of 2-(8-phthalimidooctyl)thiophene (3e) (42.7%).

Yields for syntheses of analogous intermediates (3) of varying alkyl chain lengths (n) were as follows:

2-(3-Phthalimidopropyl)thiophene (3m). 64.6 gm (82.6%)

2-(4-Phthalimidobutyl)thiophene (3b). 6.8 gm (55.3%), 8.7 gm (74.4%)

2-(5-Phthalimidopentyl)thiophene (3n). 28.9 gm (64.5%), 63.1 gm (58.9%)

2-(6-Phthalimidohexyl)thiophene (3c). 2 gm (64.5%), 15 gm (59%), 3 gm (79.8%)

2-(7-Phthalimidoheptyl)thiophene (3d). 5 gm (84.7%), 7 gm (79.8%)

2-(9-Phthalimidononyl)thiophene (3o). 33 gm (36.4%)

2-(10-Phthalimidodecyl)thiophene (3f). 12 gm (67.8%)

2-(12-Phthalimidododecyl)thiophene (3g). 10.7 gm (33.8%), 9 gm (39.6%)

5-Methyl-2-(4-Phthalimidobutyl)thiophene (3h). 2 gm (77.8%), 20 gm (66.2%)

5-Methoxy-2-(4-Phthalimidobutyl)thiophene (3i). 1.8 gm (62.1%), 16.9 gm (67.1%)

5-Methylmercapto-2-(4-Phthalimidobutyl)thiophene (3j). 4 gm (31.7%)

Step 3. In this step, the mono- or disubstituted synthetic intermediate 2-thienylalkylamine (4) was synthesized from 3. To synthesize 4e, 2-(8-phthalimidooctyl)thiophene (3e) from step 2 (8.45 gm, 0.0247 moles) and hydrazine hydrate (2.8 mL, 0.0494 moles) were added to ethanol (50 mL). The mixture was heated to reflux for 4 hours and stirred at room temperature for 12 hours. The contents were diluted with 1 M HCl (25 mL) and conc. HCl was added dropwise to lower the pH to 2. The white suspension was heated to 50° C. for 20 minutes to complete the hydrolysis. The cooled suspension was filtered and the filtrate was concentrated under reduced pressure to remove the ethanol and water. The residue was diluted with water (10 mL) and adjusted to pH 9–10 with sodium carbonate. Potassium chloride was added to reduce the solubility of the amine. The resulting mixture was extracted with chloroform (3×50 mL). The combined organic layers were washed with water (10 mL), dried with $MgSO_4$ (anhydrous), filtered and evaporated under reduced pressure to give 2.72 gm of 8-(2-thienyl)octylamine (4e) (52.1%).

Yields for syntheses of analogous intermediates (4) of varying alkyl chain length (n) were as follows:

3-(2-Thienyl)propylamine (4m). 26.3 gm (78.3%)

4-(2-Thienyl)butylamine (4b). 7 gm 5-(2-Thienyl)pentylamine (4n). 46.2 gm (85%)

6-(2-Thienyl)hexylamine (4c). 3 gm (86.2%), 4.6 gm (52.3%)

7-(2-Thienyl)heptylamine (4d). 1.5 gm (89.5%), 2.8 gm (70.9%)

9-(2-Thienyl)nonylamine (4o). 10.25 gm (48.2%)

10-(2-Thienyl)decylamine (4f). 4.1 gm (53.2%)

12-(2-Thienyl)dodecylamine (4g). 1.2 gm (17.3%), 6 gm (61.5%)

2-(4-Aminobutyl)-5-methylthiophene (4h). 10 gm (88.5%)

2-(4-Aminobutyl)-5-methoxylthiophene (4i). 2 gm (40.8%), 3 gm (30.2%)

2-(4-Aminobutyl)-5-methylmercaptothiophene (4j). 2 gm (83%)

Step 4. This step was used to complete the synthesis of 2-monosubstituted or 2,5-disubstituted thienylalkylisothiocyanate (5). To synthesize T8ITC (5e), (2-thienyl) octylamine (4e) from step 3 (2.72 gm, 0.0129 moles) in dichloromethane (25 mL) and sodium hydroxide solution (50 mL, 5%) were added simultaneously to a well-chilled solution of thiophosgene (0.98 mL, 0.013 moles) in dichloromethane (50 mL). The two phase system was stirred for an additional hour at room temperature. The two layers were separated and the aqueous layer was extracted with chloroform (3×10 mL). The combined organic layers were washed with water (10 mL), dried over $MgSO_4$ (anhydrous), filtered, and evaporated under reduced pressure. The crude isothiocyanate was purified by column chromatography (silica gel, 1% ethyl acetate in hexanes) to give 0.4 gm of 8-(2-thienyl) octylisothiocyanate (5e) (11%).

Yields for syntheses of analogous intermediates (5) of varying alkyl chain lengths (n) were as follows (in the case of 5a, the precurser 2-thienylethylamine 4a was not synthesized as in step 3 but was purchased from Aldrich, Milwaukee, Wis.).

2-(2-Thienyl)ethylisothiocyanate (5a). 2 gm (75.5%)

3-(2-Thienyl)propylisothiocyanate (5m). 8.85 gm (26%)

4-(2-Thienyl)butylisothiocyanate (5b). 2 gm (39.2%), 3 gm (33.8%)

5-(2-Thienyl)pentylisothiocyanate (5n). 16.6 gm (58%)

6-(2-Thienyl)hexylisothiocyanate (5c). 0.55 gm (14.9%), 0.8 gm (14.3%)

7-(2-Thienyl)heptylisothiocyanate (5d). 0.67 gm (36.4%), 0.5 gm (14.9%)

9-(2-Thienyl)nonylisothiocyanate (5o). 0.54 gm (4.4%)

10-(2-Thienyl)decylisothiocyanate (5f). 1.1 gm (22.6%)

12-(2-Thienyl)dodeclylisothiocyanate (5g). 0.4 gm (11.5%), 0.5 gm (21.7%)

4-(5-Methyl-2-Thienyl)butylisothiocyanate (5h). 1 gm (10%)

4-(5-Methoxy-2-Thienyl)butylisothiocyanate (5i). 0.1 gm (2.8%)

4-(5-Methylmercapto-2-Thienyl)butylisothiocyanate (5j). 0.1 gm (4.1%)

The purity of the starting materials, intermediates, and final products of synthetic reactions in the Examples were checked by TLC, GC, or HPLC. The structures of the target compounds were confirmed by spectroscopic analysis (MS and $^1$H NMR). The presence of the thienyl moiety in the products was readily confirmed by the characteristic signals of the pseudoaromatic protons in $^1$H NMR spectra ($\delta$6.7–7.3) using a Varian 300 MHz NMR spectrometer; the solvent used was $CDCl_3$; and chemical shifts ($\delta$) were determined with reference to tetramethylsilane (TMS). The methylene protons signals were readily assigned according to their chemical shifts and coupling patterns. The molecular weights of the synthetic TAITCs were confirmed by electrospray ionization-mass spectrometry (EI-MS).

Example III

Synthesis of 2-Thienyl Alkyl Isothiocyanates (2-TAITCs) from 2-Thienyl Lithium via Azide Intermediates

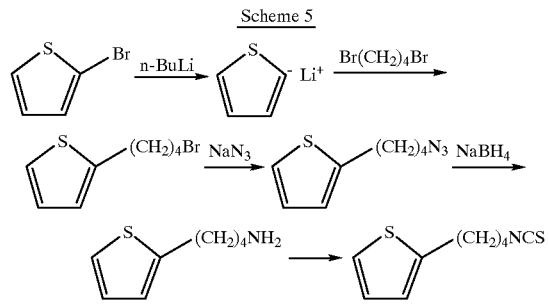

Scheme 5

2-Thienyl butyl isothiocyanate (2-TBITC). 2-Thienyl lithium can be generated from 2-bromothiophene (Aldrich Chemical Co.) and n-butyl lithium (Aeros Organics, Pittsburgh, Pa.). 2-Thienyl lithium is allowed to react with 1.5 equivalents of 1,4-dibromobutane (Aeros Organics, Pittsburgh, Pa.) to give bromobutyl thiophene. The bromine is then replaced by an azide ion. The thienyl butyl azide thus obtained is reduced by sodium borohydride to yield the amine, 2-thienyl butyl amine (Scheme 5). The 2-thienyl butyl amine dissolved in water is added dropwise to a solution of thiophosgene in dichloromethane. In another dropping funnel a solution of 10% sodium hydroxide is introduced slowly to maintained alkalinity of the reaction mixture. The reaction is allowed to stand at room temperature for an additional hour with stirring. The organic layer is separated and washed with water, saturated sodium chloride solution, water, and dried over anhydrous magnesium sulfate. The solvent is removed in vacuo and the product, 2-TBITC, obtained by vacuum distillation.

Example IV

Synthesis of 3-Thienyl Methyl Isothiocyanates (3-TMITC) from Thiophene

The 3-thienyl methyl amine can be generated using the above reaction shown in Scheme 6. It can then be converted to 3-TMITC using thiophosgene, using procedures similar to those described for in preceding examples.

Example V

Synthesis of 3-Thienyl Methyl Isothiocyanates (3-TMITC) from 3-Hydroxymethylthiophene

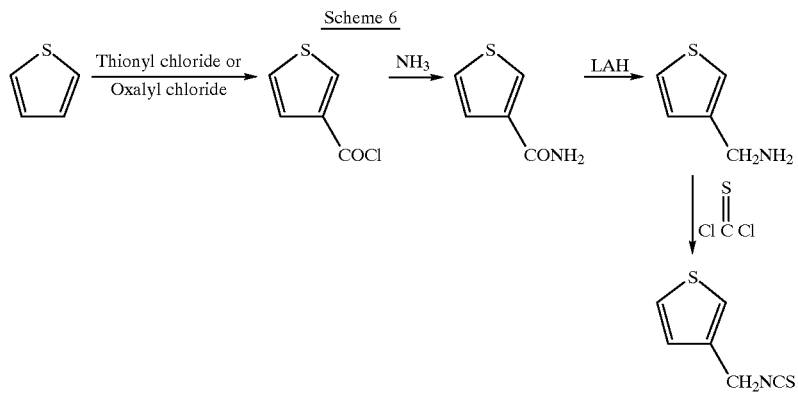

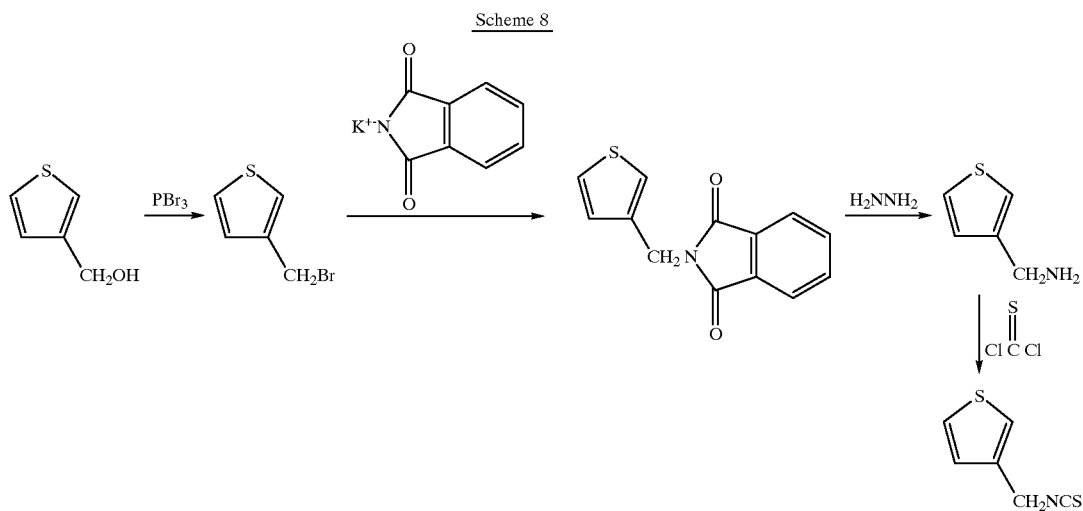

The 3-thienyl methyl amine can be generated using the reaction in Scheme 7. The 3-thienyl methyl amine was then converted to 3-TMITC using thiophosgene using procedures similar to those described in preceding examples.

Example VI

Synthesis of 3-Thienyl Methyl Isothiocyanates (3-TMITC) from 3-Carboxaldoxime

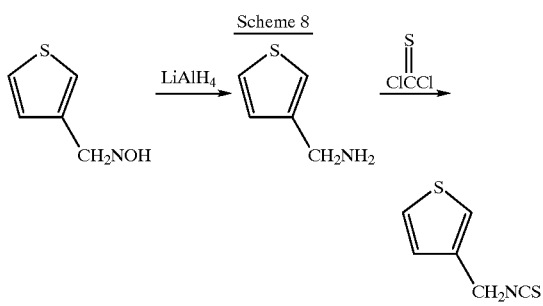

3-Thienyl methyl isothiocyanate. Thiophene-3-carboxaldoxime (Lancaster Synthesis, Windham, N.H.) was reduced with lithium aluminum hydride to yield desired 3-thienyl methyl amine in excellent yield, according the Scheme 8. The 3-thienyl methyl amine was then converted to 3-TMITC using thiophosgene using procedures similar to those described for 2-TMITC in previous examples.

Example VII

Synthesis of 3-Thienyl Butyl Isothiocyanate (3-TBITC) from 3-Thienyl Lithium via Azide Intermediate

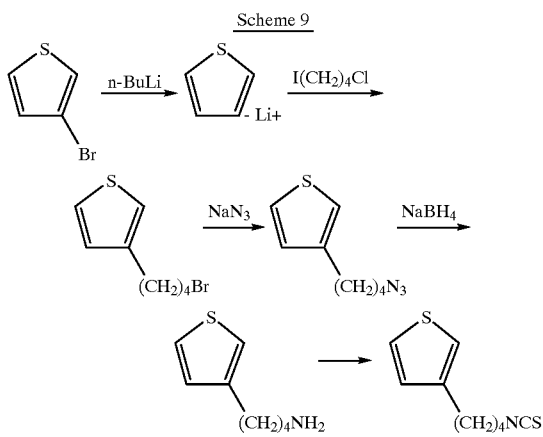

3-Thienyl butyl isothiocyanate (3-TBITC). 3-Thienyl lithium was generated from 3-bromothiophene and n-butyl lithium at −70° C. To the 3-thienyl lithium was then added an excess of 1-chloro-4-iodobutane at dry ice-acetone temperature. Upon slow warm up to room temperature a mixture of 2 and 3-thienyl butylchloride were obtained. The mixture was converted to the 2- and 3-thienyl butyl amines via the azide intermediates (Scheme 9) as described for the synthesis of 2-thienyl butyl amine, then reacted with thiophosgene to give the desired product, 3-TBITC, in low yield. The 2 isomers were separated by preparative liquid chromatography using a recycling mode. The 3-TBITC was obtained in 97% purity.

Example VIII

GST-Inducing Activity of 2-TMITC, 3-TMITC, 2-TBITC, 3-TBITC, FBITC and SBITC

Introduction: Correlation of GST induction with chemopreventive activity. The phase II enzyme glutathione sulfotransferase (GST) is commonly induced by inhibitors of carcinogenesis. GST is one of the enzymes in a major detoxifying system; it catalyzes the conjugation of a wide variety of reactive electrophiles with glutathione. These less toxic, water soluble conjugates can then be readily eliminated from the body by excretion. Because most ultimate carcinogenic forms of chemical carcinogens are electrophiles, induction of GST activity is recognized as a major mechanism of action of many chemopreventive agents in carcinogen detoxification. Positive correlation between the inhibitory activity of anticarcinogens and their ability to induce increased GST activity is well established; many classes of compounds have been found that inhibit chemical carcinogenesis and also induce increased GST enzyme activity significantly (*Nutr. Cancer* 17:19–26 (1992)). The glutathione S-transferase assay is thus an extremely useful rapid prescreening tool for inhibitors of carcinogenesis.

Materials and methods. Female A/J mice from Harlan Sprague-Dawley (Indianapolis, Ind.), 7 weeks old, were fed a semipurified (AIN76A) diet from ICN Nutritional Biochemicals (Cleveland, Ohio) for one week prior to and throughout the entire duration of the experiment. Animals were housed in temperature controlled animal quarters with a 12/12 hour light/dark cycle. Water was given ad libitum. The animals were cared for by trained animal technicians.

The test compounds were synthesized as described in the preceding examples; the furyl and selenyl analogs were synthesized using essentially the same synthetic methods used for the thienyl compounds. The test compounds were administered by oral intubation (i.e., gavage) of 2 or 4 mg of the compound in the female A/J mice in 0.3 mL cottonseed oil, every other day for a total of three treatments. This represented approximately 0.2–0.6 mmol test compound per kg of body weight. Control groups were given only cottonseed oil. The reference compound used was phenylbutylisothiocyanate (PBITC). The mice were sacrificed twenty-four hours after the last dose. The number of animals, dosages, and assay results are shown in Tables Ia and Ib.

Procedures used for the preparation of cytosolic fractions from the liver, lung, forestomach, small and large bowel mucosa of laboratory animals are essentially those described previously (L. Lam et al., *Nutr. Cancer.* 12:43–47 (1989), incorporated herein by reference in its entirety). The liver, lung, forestomach, and the mucosa from the proximal ⅓ of the small intestine and the entire length of the large intestine including the caecum were removed. The tissues were homogenized in cold 1.15% KCl (pH 7.4). The homogenate was centrifuged at 9,000×g for 20 min. and the supernatant was centrifuged at 100,000×g for one hour. The cytosolic fractions were kept frozen at −80° C. until use. The protein concentration of these samples was determined by the method of Lowry et al (*J. Biol. Chem.,* 193: 265 (1951)).

The activity of cytosolic GST was assayed according to the method of Habig et al. using 1-chloro-2,4-dinitrobenzene (CDNB) as the substrate (W. Habig, et al., *J. Biol. Chem.,* 249: 712 (1974)). The complete assay solution contained, in a total volume of 2.0 mL, 0.1 M phosphate buffer, pH 6.5, 5 mM glutathione, 1 mM CDNB, and 20 µL of the cytosol. The reaction was monitored at 340 nm in a Beckman model DU65 UV-VIS spectrophotometer. Assays were performed at 30° C. Complete assay mixture without the cytosolic enzyme was used as the reference blank. Specific activity of GST was calculated in micromoles of glutathione conjugates per minute per milligram of protein. Data were analyzed by the Student's "t" test and P values were obtained in comparison to the control (see Table Ia and Table Ib). In this method, a compound that has greater than 40% and 80% GST increase in the liver and small bowel mucosa, respectively, over the control level, is generally regarded as worth further investigation. This percentage increase corresponds to T/C (test extract/vehicle control) ratio for GST specific activity of 1.40 and 1.80, respectively.

lower equivalent dose (2 mg, 0.53 mmol/kg body weight). The difference in GST activity was most noticeable in the small bowel (T/C, 2-TMITC=4.58, 3-TMITC=4.24, PBITC=2.39) and in the forestomach (T/C, 2-TMITC=2.04, 3-TMITC=2.94, PBITC=1.05). With a virtually identical dose, 2-TBITC was found to be either as active or more so in different tissues of mice. For example, in the liver, the T/C ratio was 1.52 for 2-TBITC and 1.07 for PBITC; in the small bowel, they were 3.00 and 2.85, respectively. At approximately $\frac{1}{3}$ of the dose (0.2 mmol/kg body weight), the induction of GST was comparable for both TBITCs and PBITC. At this dose level, the induction of enzyme activity in the small bowel was found to be only 40–74% above the TABLE Ia Effect of 2- & 3-thienyl alkylisothiocyanate on the activity of glutathione S-transferase in female A/J mice

| Chemicals[a] | Dosage[b] (mg) | No. of animals | Liver GST Spec. Act.[c] | Ratio[d] | Small Bowel Mucosa GST Spec. Act.[c] | Ratio[d] | Forestomach GST Spec. Act.[c] | Ratio[d] | Lung GST Spec. Act.[c] | Ratio[d] | Large Bowel Mucosa GST Spec. Act.[c] | Ratio[d] |
|---|---|---|---|---|---|---|---|---|---|---|---|---|
| Control | 0 | 4 | 1.01 ± 0.12 | | 0.33 ± 0.02 | | 0.80 ± 0.06 | | 0.42 ± 0.04 | | 0.31 ± 0.01 | |
| PBITC | 2 | 4 | 1.11 ± 0.05 | 1.10 | 0.79 ± 0.18e | 2.39 | 0.84 ± 0.05 | 1.05 | 0.33 ± 0.12 | 0.79 | 0.36 ± 0.02[f] | 1.16 |
| 2TMITC | 2 | 4 | 1.29 ± 0.13[f] | 1.28 | 1.51 ± 0.31[e] | 4.58 | 1.63 ± 0.77[f] | 2.04 | 0.43 ± 0.03 | 1.02 | 0.40 ± 0.06 | 1.29 |
| 2TMITC | 4 | 3 | 1.30 ± 0.10[f] | 1.29 | 0.99 ± 0.34[f] | 3.00 | 1.36 ± 0.16[e] | 1.70 | 0.38 ± 0.03 | 0.90 | 0.39 ± 0.07 | 1.26 |
| 3TMITC | 2 | 4 | 1.63 ± 0.25[e] | 1.61 | 1.40 ± 0.25[e] | 4.24 | 2.35 ± 0.14[e] | 2.94 | 0.45 ± 0.03 | 1.07 | 0.34 ± 0.05 | 1.10 |
| 3TMITC | 4 | 3 | 1.24 ± 0.18 | 1.23 | 0.83 ± 0.22[e] | 2.52 | 0.99 ± 0.32 | 1.24 | 0.50 ± 0.10 | 1.19 | 0.48 ± 0.08[f] | 1.55 |
| Control | 0 | 4 | 1.27 ± 0.08 | | 0.47 ± 0.06 | | 0.85 ± 0.22 | | 0.54 ± 0.06 | | 0.29 ± 0.06 | |
| PBITC | 2 | 2 | 1.36 ± 0.17 | 1.07 | 1.34 ± 0.27[e] | 2.85 | 1.20 ± 0.32 | 1.41 | 0.51 ± 0.16 | 0.94 | 0.36 ± 0.01 | 1.24 |
| 2TBITC | 2 | 4 | 1.93 ± 0.21[e] | 1.52 | 1.41 ± 0.21[e] | 3.00 | 1.30 ± 0.17[f] | 1.53 | 0.53 ± 0.04 | 0.99 | 0.42 ± 0.06 | 1.45 |
| 2TBITC | 4 | 4 | 2.16 ± 0.40[e] | 1.70 | 1.50 ± 0.21[e] | 3.19 | 1.33 ± 0.06[f] | 1.56 | 0.68 ± 0.05 | 1.26 | 0.35 ± 0.05 | 1.23 |

[a]Abbreviations: Control, cottonseed oil; PBITC, phenylbutylisothiocyanate; 2TMITC, 2-thienylmethyl isothiocyanate; 3TMITC, 3-thienylmethyl isothiocyanate; 2TBITC, 2-thienylbutyl isothiocyanate.
[b]Administration by oral intubation of 2 or 4 mg of chemical in female A/J mice in 0.3 mL cottonseed oil, every other day for a total of three treatments. Control groups were given only cottonseed oil. The mice were sacrificed twenty-four hours after the last dose.
[c]μmoles of glutahione conjugates/min/mg of protein.
[d]Test extract/vehicle control.
[e]Statistical analysis by Student's t-test, test versus control; $P < 0.005$.
[f]Statistical analysis by Student's t-test, test versus control; $P < 0.05$.

TABLE 1b

Effects of chemopreventive chemicals of glutathione-S-transferase activity in female A/J mice

| Group no. | Chemical[a] | Dose (mmol/kg) | Liver | Lung | SBM | Colon | Forestomach |
|---|---|---|---|---|---|---|---|
| 1 | none | — | 1.36 ± 0.23[b] | 0.37 ± 0.02 | 0.24 ± 0.03 | 0.47 ± 0.02 | 0.67 ± 0.10 |
| 2 | TBITC[c] | 0.80 | 2.04 ± 0.69 | 0.26 ± 0.08[d] | 0.65 ± 0.17[f] | 0.43 ± 0.06 | 0.96 ± 0.10[f] |
| 3 | | 0.40 | 1.60 ± 0.18 | 0.38 ± 0.03 | 0.50 ± 0.06[i] | 0.43 ± 0.03[d] | 0.69 ± 0.20 |
| 4 | FBITC | 0.80 | 2.79 ± 0.22[j] | 0.41 ± 0.06 | 0.86 ± 0.14[h] | 0.47 ± 0.02 | 0.94 ± 0.09[f] |
| 5 | | 0.45 | 2.04 ± 0.14[g] | 0.46 ± 0.05[f] | 0.62 ± 0.09[h] | 0.47 ± 0.03 | 0.94 ± 0.03[f] |
| 6 | SBITC | 0.80 | 3.07 | 0.42 | 0.42 | 0.42 | 0.81 |
| 7 | | 0.45 | 3.68 ± 0.29[j] | 0.65 ± 0.06[e] | 0.59 ± 0.12[d] | 0.46 ± 0.06 | 0.81 ± 0.06[d] |

[a]The inhibitors were dissolved in 0.3 ml corn oil and administered by gavage on days 1, 3 and 5. Animals were sacrificed on day 6.
[b]Glutathione-S-transferase activity was assayed by the method of Habig, et al., and are reported as μmoles/min/mg of protein. The values are mean ± SD.
[c]Abbreviations: TBITC = Thienylbutylisothiocyanate, FBITC = Furylbutylisothiocyanate, SBITC = Selenylbutylisothiocyanate.
[d]Student's t-test was used to compare the values of test compounds versus control (Group 1). $P < 0.05$
[e]$P < 0.01$
[f]$P < 0.005$
[g]$P < 0.001$
[h]$P < 0.0005$
[i]$P < 0.0001$
[j]$P < 0.00005$
Habib, W.H., Pabst, M.J., Jakoby, W.B., J. Biol. Chem., 249:712 (1974).

Results. Table Ia shows comparative results for the thienyl compounds. At a 2 mg (0.68 mmol/kg body weight) dose, both 2- and 3-TMITC were found to be more active than the reference compound PBITC which was given at a slightly basal level. Nevertheless, it is worth pointing out that the induction profile of TBITC is as good, if not better than the reference compound, PBITC. In the large bowel, the basal GST activity is low and induction is generally not as easily obtained as that in the liver or the small bowel. In these experiments, it was found that all TAITC's were able to induce slightly elevated GST activity in this tissue. In particular, at the low dose of 0.2 mg/kg body weight, the induction was comparable to that by 2BT which is a known colon tumor inhibitor. The newly synthesized TAITC show GST-inducing potency similar to, if not better than, those of the two reference compounds.

Table Ib shows results for the furylbutylisothiocyanate (FBITC) and selenylbutylisothiocyanate (SBITC) test compounds. It is readily apparent that induction profile of the furyl- or seleno-heterocyclic test compounds was as good or better in all organs than the novel chemopreventive TBITC evaluated in Table Ia and the immediately preceding paragraph. Notably, at a 0.8 mmol/kg body weight dose, both FBITC and SBITC were found to be significantly more active in liver than TBITC which was given at an equivalent dose. In liver, the difference in GST activity between the furyl- or seleno-heterocyclic test compounds and the control, as measured by the T/C ratio, was 2.05 for FBITC and 2.26 for SBITC; in the small bowel the T/C ratio was 3.58 for FBITC and 1.75 for SBITC; and in the forestomach the T/C ratio was 1.40 for FBITC and 1.22 for SBITC.

Example IX

Tissue Sulfhydryl (TSH) and Glutathione (GSH) Inducing Activity of 2-TMITC, 3-TMITC, 2-TBITC, 3-TBITC, FBITC and SBITC Introduction. An increase in GSH levels is important in the overall detoxifying process. Not only is GSH is a mandatory substrate for GST, but GSH by itself, without the help of the enzyme, is also a very important detoxifying agent. The biosynthesis of GSH is self-regulating, therefore it is generally very difficult to induce increased level of GSH beyond 100% (i.e. T/C>2.0). This is particularly true in the liver where the pool of GSH is much larger than those in other tissues. The general level of tissue sulfhydryls (TSH) is a good measure of GSH level in tissues.

Materials and Methods. Experimental animals (female A/J mice), dosages, and methods of administration were as in Example VIII. The acid-soluble SH levels in tissue homogenates (BH) were assayed according to the method of Ellman (*Arch. Biochem. Biophys.*, 82: 70 (1959)). Aliquots of tissue homogenates were precipitated with equal volumes of 4% sulfosalicylic acid. The supernatants were assayed for the presence of free SH groups by the addition of 9× volume of Ellman's reagent [0.1 mM 5,5'-dithiobis(2-nitrobenzoic acid), DTNB] in 0.1 M sodium phosphate buffer, pH 8.0. The absorbence was recorded at 412 nm on the UV spectrophotometer.

GSH was quantitated by the method of Siller-Cepeda, et al., (*Plant Cell Physiology* 32(8) 1179–1185 (1991)). Tissue homogenates (200 µl) were diluted with an equal volume of 10% perchloric acid containing 1 mM bathophenenthrolinedisulfonic acid. After centrifugation (5000 g for 15 minutes), the pellet was washed twice with 350 µl of the perchloric acid solution. The combined supernatants were stored at −80° C. until ready for derivatization. For derivatization, samples (250 µl) were diluted with 25 µl of γ-Glu-Glu (5 mM), 25 µl of 100 mM iodoacetic acid in 0.2 mM m-cresol purple, and 350 µl 2 M KOH/2.4 M KHCO$_3$. After incubation in the dark at room temperature for 15 minutes, 500 µl of 1% 2,4-dinitro-1-fluorobenzene (DNFB) in ethanol was added, and the samples were stored at 4° C. in the dark until analyzed by high pressure liquid chromatography (HPLC). A Rainin Microsorb MV 5 µm aminopropyl (4.6 mm×25 cm) column was used with a Shimadzu SCL-10A HPLC system. The column was equilibrated for 12 minutes with 20% solvent B (solvent A=80% methanol, solvent B=0.5 mM sodium acetate in 64% methanol) at 1 ml/minute. The sample was then introduced. After the column was maintained at 20% B for 5 minutes, elution was performed with a gradient consisting of 20% to 99% B over 10 minutes, followed by 10 minutes at 99% B. The internal standard and the DNFB conjugate of GSH eluted at 15 and 16 minutes, respectively. The column was reequilibrated between injections for 12 minutes as described above. GSH was quantitated by the internal standard method using a standard curve.

Results. Results of the TSH assay are shown in Table II. At the higher doses, the induction of TSH by TAITCs was found to be similar if not better than that by PBITC. At low dose (0.2 mmol/kg), the 2 TBITCs were found to induce TSH in the liver, forestomach and the lung. These results, together with other observations, suggested that the high dose that was used in these experiments appeared to be reaching the toxicity level of these compounds.

Results of the GSH assay are shown in Table III. At the higher doses, GSH was induced by TBITC in the liver, small bowel mucosa, and colon. FBITC performed even better in these tissues and also induced GSH in the lung. The lower dose of SBITC was more effective than the higher dose in inducing GSH in liver, lung and colon tissues. Overall, GSH induction was favorable for all three test compounds.

TABLE II

Effect of 2- & 3-thienyl alkylisothiocyanate on the tissue s7ulfhydral levels in female A/J mice

| Chemicals[a] | Dosage[b] (mg) | No. of animals | Liver TSH Levels[c] | Ratio[d] | Small Bowel Mucosa TSH Levels[c] | Ratio[d] |
|---|---|---|---|---|---|---|
| Control | 0 | 4 | 13.54 ± 3.52 | | 5.36 ± 1.76 | |
| PBITC | 2 | 4 | 14.30 ± 1.37 | 1.06 | 6.96 ± 1.31 | 1.30 |
| 2TMITC | 2 | 4 | 14.59 ± 3.18 | 1.08 | 9.96 ± 1.18f | 1.86 |
| 2TMITC | 4 | 3 | 13.34 ± 1.89 | 0.99 | 7.46 ± 1.13 | 1.39 |
| 3TMITC | 2 | 4 | 14.13 ± 3.08 | 1.04 | 8.07 ± 1.37 | 1.51 |
| 3TMITC | 4 | 3 | 11.07 ± 2.05 | 0.82 | 7.22 ± 0.55 | 1.35 |
| Control | 0 | 4 | 14.60 ± 1.01 | | 7.71 ± 1.18 | |
| PBITC | 2 | 2 | 12.55 ± 3.40 | 0.86 | 8.84 ± 0.09 | 1.15 |
| 2TBITC | 2 | 4 | 12.09 ± 2.23 | 0.83 | 9.48 ± 0.10 | 1.23 |
| 2TBITC | 4 | 4 | 12.57 ± 1.24 | 0.86 | 10.16 ± 1.20[f] | 1.32 |

TABLE II-continued

Effect of 2- & 3-thienyl alkylisothiocyanate on the tissue s7ulfhydral levels in female A/J mice

| Chemicals[a] | Dosage[b] (mg) | No. of animals | Forestomach TSH Levels[c] | Ratio[d] | Lung TSH Levels[c] | Ratio[d] | Large Bowel Mucosa TSH Levels[c] | Ratio[d] |
|---|---|---|---|---|---|---|---|---|
| Control | 0 | 4 | 2.75 ± 0.76 | | 1.40 ± 0.74 | | 4.46 ± 0.70 | |
| PBITC | 2 | 4 | 3.63 ± 0.70 | 1.32 | 1.33 ± 0.11 | 0.96 | 4.98 ± 1.46 | 1.12 |
| 2TMITC | 2 | 4 | 4.05 ± 1.37 | 1.47 | 2.56 ± 0.33f | 1.83 | 4.16 ± 1.06 | 0.93 |
| 2TMITC | 4 | 3 | 1.92 ± 0.50 | 0.70 | 2.21 ± 0.53 | 1.58 | 5.62 ± 0.92 | 1.26 |
| 3TMITC | 2 | 4 | 2.59 ± 1.55 | 0.94 | 2.12 ± 0.44 | 1.52 | 4.68 ± 0.46 | 1.05 |
| 3TMITC | 4 | 3 | 3.66 ± 1.29 | 1.33 | 0.86 ± 0.19 | 0.62 | 5.90 ± 0.89 | 1.32 |
| Control | 0 | 4 | 5.62 ± 1.48 | | 2.19 ± 0.41 | | 2.70 ± 0.17 | |
| PBITC | 2 | 2 | 6.43 ± 2.63 | 1.14 | 2.19 ± 0.04 | 1.00 | 2.16 ± 1.01 | 0.80 |
| 2TBITC | 2 | 4 | 5.01 ± 1.74 | 0.89 | 2.58 ± 0.16 | 1.18 | 3.03 ± 1.01 | 1.13 |
| 2TBITC | 4 | 4 | 3.50 ± 1.43 | 0.62 | 2.62 ± 0.16 | 1.20 | 3.74 ± 0.86[f] | 1.39 |

[a]Abbreviations: Control, cottonseed oil; PBITC, phenylbutylisothiocyanate; 2TMITC, 2-thienylmethyl isothiocyanate; 3TMITC, 3-thienylmethyl isothiocyanate; 2TBITC, 2-thienylbutyl isothiocyanate.
[b]Administration by oral intubation of 2 or 4 mg of chemical in female A/J mice in 0.3 mL cottonseed oil, every other day for a total of three treatments. Control groups were given only cottonseed oil. The mice were sacrificed twenty-four hours after the last dose.
[c]$\mu$moles of tissue sulfhydral groups/g of wet liver weight.
[d]Test extract/vehicle control.
[e]Statistical analysis by Student's t-test, test versus control; $P < 0.005$.
[f]Statistical analysis by Student's t-test, test versus control; $P < 0.05$.

TABLE III

Effects of chemopreventive chemicals of glutathione (GSH) levels in female A/J mice

| Group no. | Chemical[a] | Dose (mmol/kg) | Liver | Lung | SBM | Colon | Forestomach |
|---|---|---|---|---|---|---|---|
| 1 | None | — | 4.25 ± 0.41[b] | 1.31 ± 0.22 | 2.45 ± 0.39 | 0.79 ± 0.11 | |
| 2 | TBITC[c] | 0.80 | 6.05 ± 1.77[d] | 1.03 ± 0.27 | 2.76 ± 0.21 | 1.07 ± 0.10[f] | |
| 3 | | 0.40 | 5.03 ± 0.78[d] | 1.17 ± 0.15 | 2.23 ± 0.58[d] | 0.96 ± 0.16[d] | |
| 4 | FBITC | 0.80 | 6.64 ± 1.34[e] | 1.44 ± 0.22 | 2.88 ± 0.27 | 1.09 ± 0.10[f] | |
| 5 | | 0.40 | 6.22 ± 0.57[h] | 1.26 ± 0.34 | 2.64 ± 0.30 | 0.95 ± 0.11[d] | |
| 6 | SBITC | 0.80 | 4.13 | 0.91 | 2.38 | 0.92 | |
| 7 | | 0.40 | 5.39 ± 0.44[d] | 1.56 ± 0.07[d] | 2.23 ± 0.22 | 1.09 ± 0.14[d] | |

[a]The inhibitors were dissolved in 0.3 ml corn oil and administered by gavage on days 1, 3 and 5. Animals were sacrificed on day 6.
[b]Glutathione levels were assayed by the method of Siller-Cepeda, et al., and are reported as $\mu$moles/gram wet weight. The values are ± SD.
[c]Abbreviations: TBITC = Thienylbutylisothiocyanate, FBITC = Furylbutylisothiocyanate, SBITC = Selenylbutyl-isothiocyanate.
[d]Student's t-test was used to compare the values of test compounds versus control (Group 1). $P < 0.05$
[e]$P < 0.01$
[f]$P < 0.005$
[g]$P < 0.001$
[h]$P < 0.0005$
Siller, Cepeda, Plant Cell Physiology, 32: 1179–1185 (1991).

Example X

Inhibition of NNK-Induced DNA Methylation in Mouse Lung and Liver by 2-TMITC, 3-TMITC, 2-TBITC and 3-TBITC Introduction. This assay is based on the inhibition of DNA methylation induced by 4-(Methylnitrosamino)-1-(3-pyridyl)-1-butanone (NNK) in laboratory animals (M. Morse et al., Cancer Res. 49:549 (1989)). The assay correlates with the inhibition of pulmonary adenoma formation and has been used successfully for the study of potential inhibitors of chemical carcinogenesis. NNK is the most potent carcinogenic nitrosamine so far found in tobacco and tobacco smoke (S. Hecht et al., Cancer Res. 46:498 (1986)). This compound is known to induce lung tumors in A/J mice. The degree of tumorigenesis has been correlated with the extent of $O^6$-guanine methylation of the lung DNA. Both PAITC and 2BT have been found to inhibit NNK-induced pulmonary adenoma in A/J mice.

Materials and methods. Female A/J mice 6 to 7 weeks of age, from Harlan Sprague-Dawley, Indianapolis, Ind., were acclimated one week upon arrival and then fed a semipurified diet (AIN76A) from ICN Nutritional Biochemicals (Cleveland, Ohio) for an additional week before the start and throughout the entire duration of the experiment. Animals were housed in temperature controlled (20±2° C., 50±10% relative humidity) animal quarters with a 12/12 hour light/dark cycle in the animal facilities of the University of Minnesota. Water was given ad libitum. Animals were cared for by trained animal technicians.

7-Methylguanine (7-mGua), $O^6$-methylguanine ($O^6$-mGua), guanine, and NNK were purchased from Chemsyn Science Laboratories (Lenexa, Kans.).

In a series of 3 experiments the test compounds were given by gavage (oral intubation) to the animals at low (2 mg, ~0.5–0.7 mmol/kg) or (high 4 mg, ~1–1.5 mmol/kg) doses in 0.3 mL cottonseed oil, once every two days for a total of 3 doses. It should be noted that either corn oil and cottonseed oil can be used in this and the following experiments. Two hours following the last dose, a single dose of NNK (2 mg/0.1 ml saline) was administered by i.p. injection. The mice were then sacrificed 4 hours after the injection. The control groups were given cottonseed oil and saline only. DNA is isolated from the excised livers and lungs according to the procedures in Current Protocols in Molecular Biology (K. Marmur, *J. Mol. Biol.* 3:208–218 (1961)). An aliquot of each purified hepatic DNA sample and all of each lung DNA sample was subjected to neutral thermal hydrolysis (100 ° C., 30 min) to release 7-mGua. The hydrolysates were centrifuged and the pellets hydrolyzed in 0.1 N HCl (70° C., 30 min) to release $O^6$-mGua and guanine. Pre-HPLC sample purification was accomplished by the use of Gelman Acrodiscs (Gelman Sciences, Ann Arbor, Mich.). The level of guanine and DNA adducts of $O^6$-methylguanine ($O^6$-mGua) and 7-methyl guanine (7-mGua) (mmole/mole of guanine) were quantitated using strong cation exchange HPLC column and fluorescence detection according to the method of Herron and Shank (*Anal. Chem.* 52:1228–1233 (1980)). The identities of 7-mGua, $O^6$-mGua, and guanine were confirmed by co-elution with authentic standards. The amount of $O^6$-mGua, calculated from a standard curve, can also be expressed per $10^6$ guanine bases. The significance of the experimental deviation from the control was analyzed by the student's "t" test. A P value of significance was set at <0.05.

Results. The results of the NNK-induced DNA methylation inhibition assay are shown in Table IV. At the high doses the inhibition of $O^6$-MeG formation by the TAITCs was similar in both the liver and in the lung within experimental error. At low doses, the inhibition by the TBITCs was comparable to that of PBITC, and the inhibition by the TMITC was slightly lower. Under these experimental conditions 2BT was ineffective.

*Res.*, 49: 2894 (1989); M. Morse et al., *Carcinogenesis*, 10: 1757–1759 (1989)). NNK is a powerful carcinogen that is found in tobacco and tobacco products. It is an organ-specific carcinogen that induces tumor formation in the lung regardless of the route of administration. The single dose experiment developed by Hecht and coworkers (*Carcinogenesis* 10:1901–1904 (1989)) is suitable for screening chemopreventive agents because the experimental period is less than 18 weeks.

Materials and methods. Female, A/J mice, 5 weeks of age were purchased from Jackson Laboratories, Bar Harbor, Me. This inbred strain of mice has been used extensively in the study of lung tumorigenesis in ours and other laboratories. They are very susceptible to carcinogens that induce pulmonary adenoma. The spontaneous tumor formation is generally higher than most other strains of mice.

The tobacco specific nitrosamine, NNK, was obtained from Chemsyn Science Laboratories (Lenexa, Kans.). NNK was dissolved in isotonic saline at 2 mg/0.2 mL and injected i.p. as a single dose. Vehicle control animals received a single injection of 0.2 mL isotonic saline.

The procedures for the induction of pulmonary adenomas by NNK are essentially those described by Hecht and coworkers (*Carcinogenesis*, 10:1901–1904 (1989)). The female A/J mice were divided into several groups with 10 or 20 mice per group. The semipurified diet as described in earlier examples was fed one week before the start of the inhibitor treatment and continued until the end of the treatment period. Following the TAITC treatment, the animals were fed lab chow until the end of the experiment. The test compounds (0.1 or 0.2 mmol/kg body weight) were dissolved in 0.3 mL corn oil and administered by gavage on

TABLE IV

Effect of 2- & 3-thienyl alkylisothiocyanate on the methylation of guanine by NNK in liver and lung DNA of A/J mice

| Chemicals[a] | Dosage[b] (mg) | No. of animals | Liver | | | | Lung | | |
|---|---|---|---|---|---|---|---|---|---|
| | | | $O^6$-MeG[c] | Ratio[d] | 7-MeG[c] | Ratio[d] | $O^6$-MeG[c] | Ratio[d] | 7-MeG[c] |
| NNK Control | 0 | 6 | 0.239 ± 0.07 | | 0.143 ± 0.104 | | 0.049 ± 0.010 | | N.D.e |
| PBITC + NNK | 2 | 4 | 0.085 ± 0.03 | 0.36 | 0.136 ± 0.146 | 0.95 | 0.022 ± 0.009[f] | 0.45 | N.D.[e] |
| 2TMITC + NNK | 2 | 2 | 0.157 ± 0.01 | 0.66 | 0.137 ± | 0.96 | 0.033 ± 0.016 | 0.67 | N.D.[e] |
| 2TMITC + NNK | 4 | 4 | 0.050 ± 0.03 | 0.21 | 0.119 ± 0.051 | 0.83 | 0.025 ± 0.004[f] | 0.52 | N.D.[e] |
| 3TMITC + NNK | 2 | 3 | 0.150 ± 0.03 | 0.63 | 0.149 ± 0.133 | 1.04 | 0.012 ± 0.004[f] | 0.25 | N.D.[e] |
| 3TMITC + NNK | 4 | 4 | 0.102 ± 0.00 | 0.43 | 0.098 ± 0.032 | 0.69 | 0.026 ± 0.007[f] | 0.53 | N.D.[e] |
| NNK Control | 0 | 6 | 0.159 ± 0.02 | | 0.069 ± 0.026 | | 0.055 ± 0.015 | | N.D.[e] |
| PBITC + NNK | 2 | 4 | 0.083 ± 0.02 | 0.52 | 0.054 ± 0.007 | 0.79 | 0.026 ± 0.003[g] | 0.48 | N.D.[e] |
| 2TBITC + NNK | 2 | 4 | 0.083 ± 0.01 | 0.52 | 0.060 ± 0.009 | 0.88 | 0.028 ± 0.007[g] | 0.51 | N.D.[e] |
| 2TBITC + NNK | 4 | 4 | 0.087 ± 0.01 | 0.55 | 0.060 ± 0.028 | 0.88 | 0.037 ± 0.013 | 0.68 | N.D.[e] |

[a]Abbreviations: NNK Control, 4-(methylnitrosamino)-1-(3-pyridyl)-1-butanone; PBITC, phenylbutylisothiocyanate; 2TMITC, 2-thienylmethyl isothiocyanate; 3TMITC, 3-thienylmethyl isothiocyanate; 2TBITC, 2-thienylbutyl isothiocyanate.
[b]Administration by oral intubation of 2 or 4 mg of chemical in female A/J mice in 0.3 mL cottonseed oil, every other day for a total of three treatments. Two hours after the third dose, a single dose of NNK (2 mg/0.1 mL saline) was administered by i.p. injection. The mice were sacrificed after four hours. Control groups were given only cottonseed oil and saline solution.
[c]DNA adducts of $O^6$-methylguanine of 7-methylguanine (mmole/mole of guanine).
[d]Test extract/NNK control.
[e]Not detectable by fluorescence detection.
[f]Statistical analysis by Student's t-test, test versus NNK control; P < 0.005.
[g]Statistical analysis by Student's t-test, test versus NNK control; P < 0.05.

Example XI

In vivo Inhibition of NNK-Induced Lung Tumor Formation

Introduction. The tobacco specific nitrosamine 4-(methylnitrosamino)-1-(3-pyridyl)-1-butanone (NNK)-induced pulmonary adenoma in A/J mice is a widely used tumor model that is relevant the study of inhibition of carcinogenesis of the human lung (M. Morse et al., *Cancer* days 1, 3 and 5 for a total of 3 doses. The dosages were essentially those that showed reduction of NNK-induced DNA methylation in the bioassay system. On day 5, 2 mg NNK in 0.1 mL normal saline was administered by i.p. injection two hours after the last dose of inhibitor. Sixteen weeks after NNK administration the mice were sacrificed and necropsied. The lungs were fixed in formalin and the number of adenoma nodules were counted under the dissecting microscope. Adenoma were confirmed by histopathological examination.

Results. The results of the study of TAITC inhibition of NNK-induced lung tumorigenesis are shown in Table VII. The tobacco-specific nitrosamine, NNK, treated control group had 14.2 tumors per mouse with 100% of the mice with tumors. BT-treated groups at 0.1 and 0.2 mmol/kg b.w., as expected, did not show any protection. The number of tumors per mouse was found to be 11.8 and 11.8 with 100% of the mice developed tumors. PBITC, a known chemopreventive in the lung, had 1.9 and 1.3 tumors per mouse, respectively in the 0.1 and 0.2 mmol/kg b.w. groups. The number of mice with tumors were 80 and 65%, respectively. The new compound, TBITC, was found to exert protection at 0.1 and 0.2 mmol/kg b.w. against NNK. The tumors per mouse in these groups were 4.3 and 3.0 and the % of mice with tumors were 90 and 70%, respectively.

These results together with those in the colon show TBITC to be an effective chemopreventive agent both in the lung and the colon.

gen treatment. They are present only in the colons of carcinogen-treated animals in a dose dependent manner; the control animals do not develop abnormal lesions.

A number of chemopreventive agents have been observed to reduce AC formation in the colon of CF1 mice (L. Lam et al., Carcinogenesis 12:2311–2315 (1991)). Colon AC were induced by 1,2-dimethylhydrazine (DMH) in CF1 mice. The known inhibitor 3-butyl-4-hydroxyanisole (BHA) reduced DMH-induced average AC formation by 10 and 46% at 1 and 4 mg per dose, respectively. The inhibitors, 2BT and phenyl propyl isothiocyanate (PPITC), were found to reduce DMH-induced average AC formation by 34 and 40%, respectively. Since both BHA and 2BT have been determined previously to be inhibitors of colon carcinogenesis (L. Lam et al., Chap. 22 in *Sulfur Compounds in Foods*, C. Mussinan et al., Ed., *ACS Symposium Series* 564, 278–291 (1994)), PPITC is also expected to be effective as a colon tumor preventive agent. Thus the inhibition of AC formation is positively correlated with chemopreventive agents that are effective in the colon.

Materials and methods. Female $CF_1$ mice, 3 weeks of age, were purchased from Harlan Sprague-Dawley, Indianapolis,

TABLE VII

Effects of chemopreventive chemicals on NNK-induced lung tumor formation in female A/J mice

| Group no. | Chemicals[a] | No. of animals | Inhibitor Dose (mmol/kG) | % of mice[b] with Tumors | Tumors[c] per mouse | Tumors per Tumor-bearing Mouse |
|---|---|---|---|---|---|---|
| 1 | none[d] | 10 | 0 | 10 | 0.1 ± 0.1[e] | 1.0 |
| 2 | BT | 9 | 0.2 | 33 | 0.4 ± 0.2 | 1.3 |
| 3 | PBITC | 8 | 0.2 | 13 | 0.1 ± 0.1 | 1.0 |
| 4 | TBITC | 10 | 0.2 | 20 | 0.3 ± 0.2 | 1.5 |
| 5 | NNK | 18 | 0 | 100 | 14.2 ± 1.8 | 14.2 ± 1.8 |
| 6 | BT/NNK | 18 | 0.2 | 100 | 11.8 ± 1.0 | 11.8 ± 1.0 |
| 7 |  | 18 | 0.1 | 100 | 11.8 ± 1.3 | 11.8 ± 1.3 |
| 8 | PBITC/NNK | 17 | 0.2 | 65 | 1.3 ± 0.4 (P < 0.001) | 2.0 ± 0.4 (P < 0.001) |
| 9 |  | 20 | 0.1 | 80 | 1.9 ± 0.3 (P < 0.001) | 2.3 ± 0.2 (P < 0.001) |
| 10 | TBITC/NNK | 20 | 0.2 | 70 | 3.0 ± 0.9 (P < 0.001) | 4.2 ± 0.9 (P < 0.001) |
| 11 |  | 20 | 0.1 | 90 | 4.3 ± 1.0 (P < 0.001) | 4.7 ± 0.8 (P < 0.001) |

[a]The inhibitors were dissolved in 0.3 ml corn oil and administered by gavage on days 1, 3 and 5, two hours after administration of inhibitor, 2.0 mg of NNK in 0.1 ml normal saline was administered by i.p. injection. Animals were sacrificed 16 weeks after carcinogen administration.
[b]$\chi^2$ analysis was used to compare % of mice with tumors in groups 6–11 with group 5.
[c]Student's t-test was used to compare the tumors per mouse values in groups 6–11 with group 5.
[d]Abbreviations: NNK = 4-(N-methyl-N-nitrosamino)-1-(3-pyridyl)-1-butanone, BT = 2-n-butylthiophene, PBITC = phenylbutylisothiocyanate, TBITC = thienylbutylisothiocyanate.
[e]The values are mean ± SE

Example XII

Inhibition of DMH-Induced Colon Aberrant Crypt (AC) Formation

Introduction. This assay directly evaluates the potential of the test compounds as inhibitors of colon tumorigenesis by measuring the reduction of preneoplastic or neoplastic changes that precede tumor formation. The use of precancerous lesions termed "aberrant crypts" (AC) as a marker for colon carcinogenesis was first developed by Bird (*Cancer Letters* 37:147–151 (1987)). Upon treatment with a colon carcinogen (e.g., 1,2-dimethylhydrazine (DMH)) mice and rats develop early preneoplastic changes in the crypts of the colon that are easily observable under light microscope after methylene blue staining. These changes have all the characteristics of dysplasia which is a precancerous state that leads to malignancy through the dysplasia-carcinoma sequence. Histological examination of AC foci confirmed their dysplasia nature. They have been called microadenomas and are considered precursors to colon cancer (R. Bird et al., *Cancer Surveys* 8:189–200 (1989)). AC require less than 2 weeks to form in the mouse colon after carcino- Ind. They were housed in temperature and humidity-controlled animal quarters with a 12 hour light/dark cycle and fed AIN 76A semipurified diet until the end of the experiment. Water was given ad libitum.

Test compounds PBITC, 2-BT, 2-TMITC, 3-TMITC, 2-TBITC and 3-TBITC (0.5 mmol/kg body weight in 0.3 mL cottonseed oil) were given by gavage to the mice for the 1st two consecutive days, then every other day thereafter for a total of five treatments. (No treatment was given at the post initiation period because of lack of sufficient quantity of 3-TBITC available). On the 4th and 8th days, 0.4 mg dimethylhydraziine (DMH) in 0.2 ml EDTA-saline (pH 6.5) was given by gavage. The control groups were given cottonseed oil and/or EDTA-saline only. The mice were sacrificed 21 days following the first dose of DMH, and their colons removed. The procedures for the determination of aberrant crypts were those reported by Bird (R. Bird, *Cancer Letters* 37:147–151 (1987)). Briefly, the mouse colon including the caecum was removed, rinsed with PBS and opend longitudinally. The colon contents were removed by washing with PBS. The colon was spread mucosal side up on a piece of filter paper and fixed in buffered formalin over night. It was then stained with 0.2% methylene blue in PBS for 60 min. The AC foci were read under light microscope. The AC were topographically distinguished by their increased size, increased pericryptal zone, thicker and deeply-stained epithelial lining compared to normal crypts. The number of foci and AC in the colorectal and caecal parts of the colon were recorded separately. The significance of the data was determined by the analysis of variance method. The significance of the incidence of aberrant crypts bearing animals was analyzed by the $\chi^2$ test. The aberrant crypts were examined histologically to verify the dysplastic nature of the changes in animals treated with carcinogens and those treated with carcinogens and inhibitors.

In previous experiments, 2BT at 20 and 40 $\mu$mol per dose was found to inhibit both AC and colon tumor formation. The inhibition of ACF/colon and AC/colon by 2- and 3-TMITC and 3-TBITC were similar to those of 2BT, except that the % of animals bearing AC was reduced by 27% in the 3-TMITC group. The most active inhibitor in this experiment was found to be 2-TBITC. The ACF/colon and AC/colon were reduced to 2.6 and 3.0, respectively, compared to 9.7 for the control. The most significant inhibition was the % of animals bearing AC. It was reduced by more than 41%. Thus, it can be concluded that 2-TBITC was found to be more active than either of the parent reference compounds as inhibitors of colon AC formation.

TABLE V

Effects of 2- & 3-thienyl alkylisothiocyanate on DMH-induced aberrant crypts formation in the colon of female $CF_1$ mice.

| Chemcials[a] | Dosage[b] (mmol, mg) | No. of animals | Total ACF[c] | ACF/Colon | ACF/AC bearing animals | Total no. of AC[d] | AC/Colon | AC/Focus | % animals bearing AC |
|---|---|---|---|---|---|---|---|---|---|
| Control | — | 5 | 0 | 0 | 0 | 0 | 0 | 0 | 0 |
| PBITC | 0.5 | 3 | 0 | 0 | 0 | 0 | 0 | 0 | 0 |
| 2-BT | 0.5 | 5 | 0 | 0 | 0 | 0 | 0 | 0 | 0 |
| 2TMITC | 0.5 | 5 | 0 | 0 | 0 | 0 | 0 | 0 | 0 |
| 3TMITC | 0.5 | 5 | 0 | 0 | 0 | 0 | 0 | 0 | 0 |
| 2TBITC | 0.5 | 4 | 0 | 0 | 0 | 0 | 0 | 0 | 0 |
| 3-TBITC | 0.5 | 5 | 0 | 0 | 0 | 0 | 0 | 0 | 0 |
| DMH | —, 0.4 | 21 | 203 | 9.7 ± 4.2 | 9.7 | 247 | 11.8 ± 4.9 | 1.2 ± 0.2 | 100 |
| PBITC-CMH | 0.5, 0.4 | 2 | 26 | 13.0 ± 4.2 | 13.0 | 29 | 14.5 ± 4.9 | 1.1 ± 0.0 | 100 |
| 2-BT-DMH | 0.5, 0.4 | 15 | 116 | 7.7 ± 6.8 | 7.7 | 134 | 8.9 ± 8.1 | 1.2 ± 0.1 | 100 |
| 2TMITC-DMH | 0.5, 0.4 | 13 | 78 | 6.0 ± 3.2[e] | 6.0 | 113 | 8.7 ± 5.5 | 1.4 ± 0.2 | 100 |
| 3TMITC-DMH | 0.5, 0.4 | 11 | 66 | 6.0 ± 6.4 | 8.3 | 74 | 6.7 ± 7.3 | 1.1 ± 0.5 | 72.7 |
| 2-TBITC-DMH | 0.5, 0.4 | 12 | 31 | 2.6 ± 2.6[e] | 4.4 | 36 | 3.0 ± 3.1[e] | 1.2 ± 0.6 | 58.3[f] |
| 3-TBITC-DMH | 0.5, 0.4 | 7 | 51 | 7.3 ± 4.4 | 7.3 | 56 | 8.0 ± 4.7 | 1.1 ± 0.2 | 100 |

[a]Abbreviations: Control, cottonseed oil; PBITC, phenylbutylisothiocyanate; 2-BT, 2-N-butyl thiophene; 2TMITC, 2-thienyl methyl isothiocyanate; 3TMITC, 3-thienyl methyl isothiocyanate; 2TBITC, 2-thienyl butyl isothiocyanate, 3-TBITC, 3-thienyl butyl isocyanate; DMH, 1,2 dimethylhydrazine.
[b]Administration by oral intubation of 0.5 mmol (0.3 mL cottonseed oil)/kg weight for the 1st two consecutive days, then every other day thereafter for a total of five treatments. On the 4th and 8th day, 0.4 mg DMH in 0.2 ml EDTA-saline (pH 6.5) was give by gavage. Control groups were given cottonseed oil or EDTA-saline only. The mice were sacrificed 21 days following the 1st dose of DMH.
[c]ACF = aberrant crypts foci.
[d]AC = abernant crypts.
[e]Statistical analysis by Student's t-test, test versus control; $P < 0.05$.
[f]Statistical analysis by $\chi^2$, test versus control; $P < 0.05$.

Results. The results of the DMH-induced colon AC formation study are shown in Table V. No AC were found in the cottonseed oil vehicle control animals or those treated with the inhibitors only. The data of carcinogen-only (DMH-only) control indicated the presence of AC in all animals in this group (100%) with ACF/colon and AC/colon being 9.7 and 11.8, respectively. The parent isothiocyanate PBITC was very toxic; most of the animals died as a result of treatment, particularly in combination with DMH. The survival of PBITC-treated animals was only 25% compared to over 60–90% of the TAITC-treated groups. The corresponding TAITCs, in particular TBITCs, are much less toxic in both A/J mice and $CF_1$ mice. Since only two PBITC/DMH-treated animals survived, the data from this group was not reliable. Further, it is interesting to note that the 6-carbon homolog of the reference compound PBITC, namely, PHITC (the most potent inhibitor of NNK-induced lung tumorigenesis in the PAITC series), was recently shown to be a promoter of azoxymethane (AOM)-induced colon tumor formation (C. Rao et al., Cancer Res. 55:4311–4318 (1995)). The other reference compound, 2BT, showed a slight reduction of both ACF/colon (7.7) and AC/colon (8.9).

Example XIII

In vivo Inhibition of DMH-Induced Colon Tumor Formation

Introduction. Dimethylhydrazine (DMH)-induced tumors in the colon of CF1 mice is a widely used tumor model that is relevant to human colon cancer (L. Wattenberg et al., Cancer, 40:2432–2435 (1977); L. Lam et al., Chap. 22 in Sulfur Compounds in Foods, C. Mussinan et al., Ed., ACS Symposium Series 564, 278–291 (1994)). DMH is a rather colon-specific carcinogen. This model is one of the few cancer models that is available to study colon cancer. Its main disadvantage is the requirement of multiple dosing for up to 20 weeks. The total experimental period is 40 weeks.

Materials and methods. Female CF1 mice, 7 weeks of age, were purchased from the Charles River Laboratories, Wilmington, Mass. This strain of mice have been shown to give excellent colon tumors with DMH and its metabolites. Each experimental group contained between 10 and 30 mice. Mice at 10 weeks of age were fed a semipurified diet for one week before the start of and during inhibitor treatment as described above. At the end of the inhibitor treatment period, the animals were returned to normal lab chow until the end of the experiment.

The test compounds (0.1 or 0.2 mmol/kg body weight) were dissolved in 0.3 mL corn oil and administered by gavage three times per week (Monday, Wednesday and Friday) for 20 weeks. Each Thursday during that period, 0.4 mg DMH in 0.2 mL of 0.0001 M EDTA adjusted to pH 6.5 by sodium bicarbonate was administered subcutaneously to induce colon tumors in the mice. Animals were sacrificed 20 weeks after the final dose of DMH (i.e., forty weeks after the initial injection of DMH). The colorectum including the caecum was removed carefully, opened longitudinally, rinsed with PBS, spread, mucosa side up, on a piece of filter paper and fixed in 10% buffered formalin. Each colorectum was examined under stereomicroscope with eyepiece micrometer (Fisher Scientific, x3). The number of tumors that larger than 1 mm diameter was counted for each animal.

If desired, each colon tumor can then be classified into the macroscopic types suggested by Pozharisski (In V. Turusov et al., (Eds.), *Pathology of Tumors in Laboratory Animals*, IARC Sci Publ., Lyon, 99:159–198(1990)). Classification of tumors is optionally undertaken because the macroscopic types of colon tumors may reflect the type of growth and stages of tumor development, as well as the degrees of malignancy. In general, poorly differentiated tumors present infiltrative and endophytic growth. The wide base, lobulated or ulcerated surface are usually associated with progressive growth.

If desired, the lesions can also be examined histopathologically, and the histological type of each colon tumor can be classified into the categories described by Pozharisski (In V. Turusov et al., (Eds.), *Pathology of Tumors in Laboratory, Animals*, IARC Sci Publ., Lyon, 99:159–198 (1990)). Typically, tumors that are larger than 1 mm in diameter, together with surrounding tissue, are processed for paraffin-embedded sections and hematoxylin and eosin staining according to standard methods. Briefly, tissue is dehydrated by serial concentration of 80% to 100% alcohol in Autotechnicon Mono (Technicon Co. Tarrytown, N.Y.). The sections, 5 $\mu$m, are dewaxed, rehydrated, stained by hematoxylin-1 and eosin-y (Richard-Allan Medical Industries, Richland, Mich.). The pathological slides are read in random order under a light microscope (Nikon, x100, x400). The classification system reflects morphological cell differentiation, and therefore may be probative of the efficacy of chemopreventive agents. This classification system has been used to help identify chemopreventive agents active against DMH-, AOM- or methylazoxymethanol (MAM)-induced colon (e.g., L. Wattenberg, *Cancer Res.*, 41:2991–2994 (1981); L. Wattenberg *J. Natl. Cancer Inst.*, 58:395–398 (1977); L. Wattenberg, *Carcinogenesis*, 8:1971–1973 (1987)).

Results. The results of the study of TAITC inhibition of DMH-induced colon tumorigenesis are shown in Table VI. Typically the final results for each group of animals is reported in terms of the incidence of the colon tumor and the number of tumors per animal.

In this experiment, the percentage of mice with tumors in the carcinogen-only (DMH) control group was 90% with an average of 2.9 tumors per mouse. Test groups treated with BT at 0.1 and 0.2 mmol/kg b.w. were found to produce 46% and 76% of mice with tumors, with averages of 1.3 and 2.2 tumors per mouse, respectively. The other reference compound, PBITC, given at 0.1 and 0.2 mmol/kg b.w. produced 47% and 56% of mice with tumors, with averages of 2.1 and 3.2 tumors per mouse. When the animals were treated with the same doses (0.1 and 0.2 mmol/kg b.w.) of TBITC, the percentage of mice with tumors were 76% and 60%, with averages of 1.8 and 1.5 tumors per mouse, respectively. The tumors per mouse finding were highly significant with P values of <0.05 and <0.005, respectively. In addition to the reduction of colon tumorigenesis TBITC was found to have much less toxicity than PBITC. The latter compound had a survival rate of 60–65% whereas TBITC had a survival rate of 97 to 100% at the end of the experiment.

TABLE VI

Effects of chemopreventive chemicals on DMH-induced colon tumor formation in female CFI mice

| Group no. | Chemicals[a] | No. of Inhibitor animals | Dose (mmol/kG) | % of mice with Tumors | Tumors[c] per mouse | Tumor-bearing Mouse |
|---|---|---|---|---|---|---|
| 1 | None | 9 | 0 | 0 | 0 | 0 |
| 2 | BT[d] | 10 | 0.2 | 10 | 0.1 ± 0.1[e] | 1.0 |
| 3 | PBITC | 6 | 0.2 | 0 | 0 | 0 |
| 4 | TBITC | 9 | 0.2 | 11 | 0.1 ± 0.1 | 1.0 |
| 5 | DMH | 30 | 0 | 90 | 2.9 ± 0.4 | 3.2 ± 0.4 |
| 6 | BT/DMH | 21 | 0.2 | 76 | 2.2 ± 0.5 | 2.9 ± 0.5 |
| 7 | | 24 | 0.1 | 46 (P < 0.01) | 1.3 ± 0.3 (P < 0.005) | 2.8 ± 0.4 |
| 8 | PBITC/DMH | 16 | 0.2 | 56 | 3.2 ± 1.2 | 5.7 ± 1.8 |
| 9 | | 15 | 0.1 | 47 (P < 0.05) | 2.1 ± 0.9 | 4.0 ± 1.4 |
| 10 | TBITC/DMH | 25 | 0.2 | 60 (P < 0.05) | 1.5 ± 0.3 (P < 0.005) | 2.5 ± 0.4 |
| 11 | | 29 | 0.1 | 76 | 1.8 ± 0.4 (P < 0.05) | 2.3 ± 0.5 |

[a]The inhibitors were dissolved in 0.3 ml corn oil and administered by gavage on Mondays, Wednesdays and Fridays for 20 weeks. On Thursdays, 0.4 mg of DMH in 0.2 ml of 0.001 M EDTA adjusted with sodium bicarbonate to pH 6.5 was administered subcutaneously. Animals were sacrificed 20 weeks after the final dose of carcinogen.
[b]$X^2$ analysis was used to compare % of mice with tumors in groups 6–11 with group 5.
[c]Student's t-test was used to compare the tumors per mouse values in groups 6–11 with group 5.
[d]Abbreviations: DMH = N,N-dimethylhydrazine, BT = 2-n-butylthiophene, PBITC = phenylbutylisothiocyanate, TBITC = thienylbutylisothiocyanate.
[e]The values are mean ± SE

What is claimed is:

1. A compound having formula I

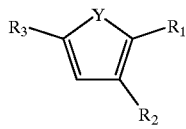

wherein:
- $R_1$ is H or (alkylene)-NCS;
- $R_2$ is H or (alkylene)-NCS;
- $R_3$ is H, (alkylene)-NCS, or a blocking group; and
- Y is Se;

provided that at least one of $R_1$, $R_2$ and $R_3$ is (alkylene)-NCS.

2. The compound of claim 1 wherein $R_3$ is a blocking group.

3. The compound of claim 2 wherein the blocking group is selected from the group consisting of an alkyl group, an aryl group, an alkoxy group, an alkylenearyl group, an alkylmercapto group, an arylalkyl group, an aryloxy group, $CX_3$, and X; wherein X is selected from the group consisting of F, Cl and Br.

4. The compound of claim 3 wherein blocking group is selected from the group consisting of $CH_3$, $OCH_3$, $SCH_3$, $CX_3$ and X wherein X is selected from the group consisting of F, Cl and Br.

5. The compound of claim 4 wherein the blocking group is selected from the group consisting of $CH_3$, $OCH_3$, $SCH_3$, $CF_3$ and F.

6. The compound of claim 1 wherein $R_1$ is H or $((C_1-C_{12})$ alkylene)-NCS; $R_2$ is H or $((C_1-C_{12})$alkylene)-NCS; and $R_3$ is H, $((C_1-C_{12})$alkylene)-NCS, or a blocking group.

7. The compound of claim 1 wherein $R_1$ is H.

8. The compound of claim 1 wherein $R_2$ is H.

9. A compound having formula I

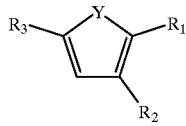

wherein:
- $R_1$ and $R_2$ are each independently (alkylene)-NCS;
- $R_3$ is H, (alkylene)-NCS, or a blocking group; and
- Y is S, O or Se.

10. The compound of claim 9 wherein $R_3$ is a blocking group selected from the group consisting of an alkyl group, an aryl group, an alkoxy group, an alkylenearyl group, an alkylmercapto group, an arylalkyl group, an aryloxy group, $CX_3$, and X; wherein X is selected from the group consisting of F, Cl and Br.

11. The compound of claim 9 wherein Y is S.

12. A compound having formula I

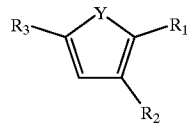

wherein:
- one of $R_1$ and $R_2$ is (alkylene)-NCS;
- the other of $R_1$ and $R_2$ is H;
- $R_3$ is (alkylene)-NCS; and
- Y is S, O or Se.

13. The compound of claim 12 wherein Y is S.

14. A compound having formula I

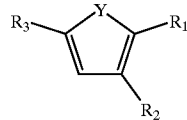

wherein:
- $R_1$ is H or $((C_7-C_{12})$alkylene)-NCS;
- $R_2$ is H or $((C_7-C_{12})$alkylene)-NCS;
- $R_3$ is H, $((C_7-C_{12})$alkylene)-NCS, or a blocking group; and
- Y is S, O or Se;

provided that at least one of $R_1$, $R_2$ and $R_3$ is $((C_7-C_{12})$alkylene)-NCS.

15. A compound having formula I

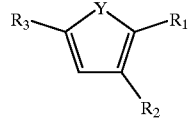

wherein:
- $R_1$ is H or (alkylene)-NCS;
- $R_2$ is H or (alkylene)-NCS;
- $R_3$ is a blocking group selected from the group consisting of $OCH_3$, $SCH_3$, $CX_3$ and F, wherein X is selected from the group consisting of F, Cl and Br; and
- Y is S, O or Se;

provided that at least one of $R_1$ and $R_2$ is (alkylene)-NCS.

16. The compound of claim 15 wherein Y is S.

17. A pharmaceutical composition formulated for use in a mammal comprising as an active ingredient a compound of formula I

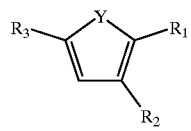

wherein:
- $R_1$ is H or (alkylene)-NCS;
- $R_2$ is H or (alkylene)-NCS;

$R_3$ is H, (alkylene)-NCS, or a blocking group; and
Y is S, O or Se;
provided that at least one of $R_1$, $R_2$ and $R_3$ is (alkylene)-NCS.

18. The pharmaceutical composition of claim 17 further comprising a pharmaceutically acceptable carrier.

19. The pharmaceutical composition of claim 17 formulated for parenteral administration to the mammal.

20. The pharmaceutical composition of claim 17 formulated for topical administration to the mammal.

21. The pharmaceutical composition of claim 17 formulated for oral administration to the mammal.

22. A pharmaceutical composition comprising:
as an active ingredient, a compound of formula I

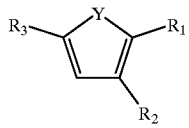

wherein:
$R_1$ is H or (alkylene)-NCS;
$R_2$ is H or (alkylene)-NCS;
$R_3$ is H, (alkylene)-NCS, or a blocking group; and
Y is S, O or Se;
provided that at least one of $R_1$, $R_2$ and $R_3$ is (alkylene)-NCS; and
a pharmaceutically acceptable salt.

23. The pharmaceutical composition of claim 22 formulated for parenteral administration.

24. A method for preventing the occurrence or progression of a cancer or a precancerous condition of the colon, lung, liver, forestomach or bowel in a mammal comprising administering to the mammal a chemopreventive composition comprising a compound of formula I

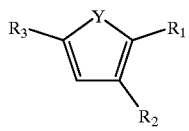

wherein:
$R_1$ is H or (alkylene)-NCS;
$R_2$ is H or (alkylene)-NCS;
$R_3$ is H, (alkylene)-NCS, or a blocking group; and
Y is S, O or Se;
provided that at least one of $R_1$, $R_2$ and $R_3$ is (alkylene)-NCS;
in an amount effective to prevent the occurrence of the cancer or precancerous condition or to slow, halt or reverse the progression of the cancer or precancerous condition.

25. The method of claim 24 wherein the chemopreventive compound is administered prophylactically to prevent the occurrence of the cancer or precancerous condition before, during or after exposure of the mammal to a known or suspected carcinogenic or procarcinogenic compound, agent or event.

26. A method for making the compound of claim 1 wherein one of $R_1$ and $R_2$ is H; the other of $R_1$ and $R_2$ is (alkylene)-NCS; $R_3$ is H or a blocking group; and Y is Se; the method comprising:

(a) providing a 5-membered heterocyclic ring having the formula

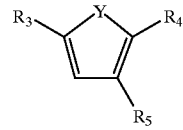

wherein $R_3$ is H or a blocking group; one of $R_4$ and $R_5$ is H; and the other of R4 and $R_5$ is (alkylene) —Br;

(b) substituting the bromide (—Br) with an amine (—NH$_2$) to yield an alkylene amine intermediate; and (c) reacting the alkylene amine intermediate with thiophosgene to yield the compound of claim 1 wherein one of $R_1$ and $R_2$ is H; the other of $R_1$ and $R_2$ is (alkylene)-NCS; $R_3$ is H or a blocking group; and Y is Se.

27. The method of claim 26 wherein step (b) comprises contacting the 5-membered heterocyclic ring with a phthalimide salt to yield a phthalimidoalkylene intermediate, followed by contacting the phthalimidoalkylene intermediate with hydrazine to yield the alkylene amine intermediate.

28. The method of claim 26 wherein step (b) comprises contacting the 5-membered heterocyclic ring with an azide salt to yield an alkylene azide intermediate, followed by contacting the alkylene azide intermediate with sodium borohydride to yield the alklyene amine intermediate.

29. A method for making the compound of claim 12 wherein $R_1$ and $R_3$ are each (alkylene)-NCS; $R_2$ is H; and Y is S, O or Se; the method comprising:

(a) providing a 5-membered heterocyclic ring having the formula

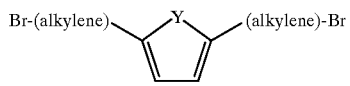

(b) substituting each bromide (—Br) with an amine (—NH$_2$) to yield a disubstituted alkylene amine intermediate; and (c) reacting the disubstituted alkylene amine intermediate with thiophosgene to yield the compound of claim 1 wherein $R_1$ and $R_3$ are each (alkylene)-NCS; $R_2$ is H; and Y is S, O or Se.

30. The method of claim 29 wherein step (b) comprises contacting the 5-membered heterocyclic ring with a phthalimide salt to yield a disubstituted phthalimidoalkylene intermediate, followed by contacting the disubstituted phthalimidoalkylene intermediate with hydrazine to yield the disubstituted alkylene amine intermediate.

31. The method of claim 29 wherein step (b) comprises contacting the 5-membered heterocyclic ring with an azide salt to yield a disubstituted alkylene azide intermediate, followed by contacting the disubstituted alkylene azide intermediate with sodium borohydride to yield the disubstituted alkylene amine intermediate.

* * * * *